US008747908B2

(12) United States Patent
Leach et al.

(10) Patent No.: US 8,747,908 B2
(45) Date of Patent: *Jun. 10, 2014

(54) MICRONIZED WOOD PRESERVATIVE FORMULATIONS

(75) Inventors: Robert M. Leach, Grand Island, NY (US); Jun Zhang, Getzville, NY (US)

(73) Assignee: Osmose, Inc., Buffalo, NY (US)

( * ) Notice: Subject to any disclaimer, the term of this patent is extended or adjusted under 35 U.S.C. 154(b) by 647 days.

This patent is subject to a terminal disclaimer.

(21) Appl. No.: 10/970,446

(22) Filed: Oct. 21, 2004

(65) Prior Publication Data
US 2005/0118280 A1    Jun. 2, 2005

Related U.S. Application Data

(63) Continuation-in-part of application No. 10/821,326, filed on Apr. 9, 2004, now Pat. No. 7,674,481.

(60) Provisional application No. 60/568,485, filed on May 6, 2004, provisional application No. 60/461,547, filed on Apr. 9, 2003, provisional application No. 60/518,994, filed on Nov. 11, 2003.

(51) Int. Cl.
| A01N 59/20 | (2006.01) |
| A01N 25/12 | (2006.01) |
| A01N 43/653 | (2006.01) |
| A01N 55/08 | (2006.01) |
| A01N 59/14 | (2006.01) |

(52) U.S. Cl.
USPC ........... 424/630; 424/489; 424/633; 424/634; 424/635; 424/638; 424/660; 514/64; 514/359; 514/383; 514/951

(58) Field of Classification Search
None
See application file for complete search history.

(56) References Cited

U.S. PATENT DOCUMENTS

| 1,388,513 | A | * | 8/1921 | Chandler | ................ | 427/291 |
| 1,999,458 | A | | 4/1935 | Hollister | | |
| 3,007,844 | A | | 11/1961 | Schulz | | |
| 3,231,464 | A | | 1/1966 | Dettwiler et al. | | |
| 3,321,464 | A | | 5/1967 | Soboczenski et al. | | |
| 3,443,881 | A | | 5/1969 | Hudson | | |
| 3,535,423 | A | * | 10/1970 | Ordas | ................ | 514/778 |
| 3,622,377 | A | | 11/1971 | Conner | | |
| 3,816,307 | A | | 6/1974 | Woods | | |
| 3,837,875 | A | | 9/1974 | Murphy | | |
| 3,945,835 | A | | 3/1976 | Clarke et al. | | |
| 3,957,494 | A | | 5/1976 | Oberley | | |
| 3,968,276 | A | * | 7/1976 | Allen | ................ | 427/297 |
| 4,003,994 | A | | 1/1977 | Downer et al. | | |
| 4,058,607 | A | | 11/1977 | Hennart et al. | | |
| 4,061,770 | A | * | 12/1977 | Marks | ................ | 514/525 |
| 4,062,991 | A | | 12/1977 | Kyte et al. | | |
| 4,075,326 | A | | 2/1978 | Kuyama et al. | | |
| 4,142,009 | A | | 2/1979 | Kyte | | |
| 4,172,904 | A | | 10/1979 | Young et al. | | |
| 4,310,590 | A | | 1/1982 | Petigara | | |
| 4,313,976 | A | | 2/1982 | Leach | | |
| 4,339,617 | A | | 7/1982 | Imai et al. | | |
| 4,404,169 | A | | 9/1983 | Ploss et al. | | |
| 4,507,152 | A | | 3/1985 | Collins et al. | | |
| 4,622,248 | A | | 11/1986 | Leach et al. | | |
| RE32,329 | E | | 1/1987 | Paszner | | |
| 4,649,065 | A | | 3/1987 | Hein et al. | | |
| 4,663,364 | A | | 5/1987 | Iwasaki et al. | | |
| 4,670,430 | A | | 6/1987 | Imamura | | |
| 4,737,491 | A | | 4/1988 | Leppavuori et al. | | |
| 4,741,971 | A | | 5/1988 | Beck | | |
| 4,808,406 | A | | 2/1989 | Brinkman | | |
| 4,857,365 | A | | 8/1989 | Hirao et al. | | |
| 4,897,427 | A | | 1/1990 | Barnavon et al. | | |
| 4,923,894 | A | | 5/1990 | Kanda et al. | | |
| 4,988,545 | A | | 1/1991 | Laks | | |
| 5,049,677 | A | | 9/1991 | Prout | | |
| 5,145,684 | A | | 9/1992 | Liversidge et al. | | |
| 5,147,686 | A | | 9/1992 | Ichimura | | |
| 5,186,947 | A | | 2/1993 | Goettsche et al. | | |
| 5,196,407 | A | | 3/1993 | Goletz et al. | | |

(Continued)

FOREIGN PATENT DOCUMENTS

| AU | 646732 | 10/1992 |
| CA | 2103470 | 8/1994 |

(Continued)

OTHER PUBLICATIONS

American Wood-Preservers' Association Standard E7-01 (2003), pp. 1-9.*

(Continued)

Primary Examiner — Abigail Fisher
Assistant Examiner — Frank Choi
(74) Attorney, Agent, or Firm — Covington & Burling LLP; Einar Stole; Melody Wu

(57) ABSTRACT

The present invention provides wood preservative compositions comprising micronized particles. In one embodiment, the composition comprises dispersions of micronized metal or metal compounds. In another embodiment, the wood preservative composition comprises an inorganic component comprising a metal or metal compound and organic biocide. When the composition comprises an inorganic component and an organic biocide, the inorganic component or the organic biocide or both are present as micronized particles. When compositions of the present invention are used for preservation of wood, the micronized particles can be observed as uniformly distributed within the wood and there is minimal leaching of the metal and biocide from the wood.

25 Claims, 8 Drawing Sheets
(2 of 8 Drawing Sheet(s) Filed in Color)

(56) References Cited

U.S. PATENT DOCUMENTS

| | | | |
|---|---|---|---|
| 5,200,421 A | 4/1993 | Ludwig et al. | |
| 5,207,823 A | 5/1993 | Shiozawa | |
| 5,277,979 A | 1/1994 | Kielbania, Jr. et al. | |
| 5,304,376 A | 4/1994 | Friedrichs et al. | |
| 5,342,438 A | 8/1994 | West | |
| 5,360,783 A | 11/1994 | Itoh et al. | |
| 5,424,077 A | 6/1995 | Lajoie | |
| 5,426,121 A | 6/1995 | Bell | |
| 5,438,034 A | 8/1995 | Walker | |
| 5,462,589 A | 10/1995 | Nicholas et al. | |
| 5,462,931 A | 10/1995 | Shaber et al. | |
| 5,484,934 A | 1/1996 | Ikeda | |
| 5,527,384 A | 6/1996 | Williams et al. | |
| 5,527,423 A | 6/1996 | Neville et al. | |
| 5,527,816 A | 6/1996 | Shaber et al. | |
| 5,536,305 A | 7/1996 | Yu et al. | |
| 5,552,378 A | 9/1996 | Trinh et al. | |
| 5,624,916 A | 4/1997 | Shaber et al. | |
| 5,635,217 A | 6/1997 | Goettsche et al. | |
| 5,667,795 A | 9/1997 | Fraley et al. | |
| 5,714,507 A | 2/1998 | Valcke et al. | |
| 5,763,364 A | 6/1998 | Frisch et al. | |
| 5,833,741 A | 11/1998 | Walker | |
| 5,874,025 A | 2/1999 | Heuer et al. | |
| 5,874,456 A | 2/1999 | McDade | |
| 5,874,476 A | 2/1999 | Hsu et al. | |
| 5,879,025 A | 3/1999 | Blumenthal | |
| 5,916,356 A | 6/1999 | Williams | |
| 5,972,266 A | 10/1999 | Fookes | |
| 5,990,043 A | 11/1999 | Kugler | |
| 6,033,648 A | 3/2000 | Candau | |
| 6,074,986 A | 6/2000 | Mulqueen et al. | |
| 6,110,263 A | 8/2000 | Goettsche et al. | |
| 6,123,756 A * | 9/2000 | Poppen et al. | 106/15.05 |
| 6,139,879 A | 10/2000 | Taylor | |
| 6,250,350 B1 | 6/2001 | Muraki et al. | |
| 6,274,199 B1 | 8/2001 | Preston et al. | |
| 6,303,183 B1 | 10/2001 | Wilczynski et al. | |
| 6,306,201 B1 | 10/2001 | Makino | |
| 6,306,202 B1 * | 10/2001 | West | 106/18.3 |
| 6,352,583 B1 | 3/2002 | Goettsche et al. | |
| 6,482,814 B1 | 11/2002 | Bath et al. | |
| 6,485,790 B2 * | 11/2002 | Walker et al. | 427/397 |
| 6,503,306 B1 | 1/2003 | Watkins | |
| 6,514,512 B1 | 2/2003 | Puterka | |
| 6,521,288 B2 | 2/2003 | Laks et al. | |
| 6,541,038 B1 | 4/2003 | Tanaka et al. | |
| 6,558,685 B1 * | 5/2003 | Kober et al. | 424/405 |
| 6,572,788 B2 | 6/2003 | Walker et al. | |
| 6,576,661 B1 | 6/2003 | Brück et al. | |
| 6,579,354 B1 | 6/2003 | West | |
| 6,585,989 B2 | 7/2003 | Herbst | |
| 6,596,246 B2 | 7/2003 | Huato et al. | |
| 6,646,147 B2 | 11/2003 | Richardson et al. | |
| 6,699,818 B1 | 3/2004 | Walter et al. | |
| 6,753,035 B2 | 6/2004 | Laks et al. | |
| 6,843,837 B2 | 1/2005 | Zhang et al. | |
| 6,849,276 B1 | 2/2005 | Dufau et al. | |
| 6,905,531 B2 | 6/2005 | Richardson et al. | |
| 6,905,532 B2 | 6/2005 | Richardson et al. | |
| 7,238,654 B2 | 7/2007 | Hodge et al. | |
| 7,316,738 B2 | 1/2008 | Richardson et al. | |
| 7,426,948 B2 | 9/2008 | Richardson et al. | |
| 7,449,130 B2 * | 11/2008 | Lloyd et al. | 252/385 |
| 8,168,304 B2 * | 5/2012 | Zhang et al. | 428/541 |
| 2001/0021711 A1 | 9/2001 | Beilfuss et al. | |
| 2001/0051175 A1 | 12/2001 | Strom et al. | |
| 2002/0003179 A1 | 1/2002 | Verhoff et al. | |
| 2002/0047058 A1 | 4/2002 | Verhoff et al. | |
| 2002/0051892 A1 | 5/2002 | Laks et al. | |
| 2002/0055046 A1 | 5/2002 | Ono et al. | |
| 2002/0128367 A1 | 9/2002 | Daisey, Jr. et al. | |
| 2003/0040569 A1 | 2/2003 | Curry et al. | |
| 2003/0060504 A1 | 3/2003 | Yoshida et al. | |
| 2003/0077219 A1 | 4/2003 | Ploss et al. | |
| 2003/0108759 A1 | 6/2003 | Roos et al. | |
| 2003/0127023 A1 | 7/2003 | Grandidier et al. | |
| 2004/0024099 A1 | 2/2004 | Narayanan et al. | |
| 2004/0050298 A1 | 3/2004 | Giger et al. | |
| 2004/0051084 A1 | 3/2004 | Wessling et al. | |
| 2004/0063847 A1 | 4/2004 | Curry et al. | |
| 2004/0176477 A1 | 9/2004 | Davison et al. | |
| 2004/0258767 A1 | 12/2004 | Leach | |
| 2004/0258768 A1 * | 12/2004 | Richardson et al. | 424/630 |
| 2004/0258838 A1 | 12/2004 | Richardson et al. | |
| 2005/0013939 A1 | 1/2005 | Venden | |
| 2005/0107467 A1 | 5/2005 | Richardson | |
| 2005/0130866 A1 | 6/2005 | Richardson et al. | |
| 2005/0152994 A1 | 7/2005 | Leach et al. | |
| 2005/0182152 A1 | 8/2005 | Nonninger et al. | |
| 2005/0249812 A1 | 11/2005 | Leach et al. | |
| 2005/0252408 A1 | 11/2005 | Richardson et al. | |
| 2005/0255251 A1 | 11/2005 | Hodge et al. | |
| 2005/0256026 A1 | 11/2005 | Hodge et al. | |
| 2005/0265893 A1 | 12/2005 | Leach et al. | |
| 2006/0062926 A1 | 3/2006 | Richardson et al. | |
| 2006/0075921 A1 | 4/2006 | Richardson et al. | |
| 2006/0075923 A1 | 4/2006 | Richardson | |
| 2006/0078686 A1 | 4/2006 | Hodge et al. | |
| 2006/0086284 A1 | 4/2006 | Zhang et al. | |
| 2006/0086841 A1 | 4/2006 | Richardson et al. | |
| 2006/0112850 A1 | 6/2006 | Zhang et al. | |
| 2006/0147632 A1 | 7/2006 | Zhang et al. | |
| 2006/0257578 A1 | 11/2006 | Zhang et al. | |
| 2006/0288904 A1 | 12/2006 | Leach et al. | |
| 2007/0021385 A1 | 1/2007 | Zhang et al. | |
| 2007/0131136 A1 | 6/2007 | Zhang et al. | |
| 2007/0193473 A1 | 8/2007 | Zhang et al. | |
| 2007/0259016 A1 | 11/2007 | Hodge et al. | |
| 2008/0199525 A1 | 8/2008 | Leach et al. | |
| 2008/0199535 A1 | 8/2008 | Taylor et al. | |
| 2008/0210121 A1 | 9/2008 | Zhang et al. | |
| 2008/0213608 A1 | 9/2008 | Richardson et al. | |
| 2008/0260841 A1 | 10/2008 | Leach et al. | |
| 2008/0286380 A1 | 11/2008 | Zhang et al. | |
| 2009/0028917 A1 | 1/2009 | Leach et al. | |
| 2009/0035564 A1 | 2/2009 | Leach et al. | |

FOREIGN PATENT DOCUMENTS

| | | |
|---|---|---|
| CA | 2251534 | 10/1997 |
| DE | 1531868 | 11/1978 |
| DE | 41 12 652 | 10/1992 |
| DE | 41 12 652 A1 | 10/1992 |
| EP | 0 472 973 | 3/1992 |
| EP | 0 472 973 A1 | 3/1992 |
| EP | 1 034 903 | 9/2000 |
| EP | 1 034 903 A1 | 9/2000 |
| GB | 222268 | 10/1924 |
| GB | 812408 | 4/1959 |
| GB | 822869 | 11/1959 |
| GB | 1 491 330 | 11/1977 |
| JP | 60-155403 | 8/1985 |
| JP | 61-244502 | 10/1986 |
| JP | S61-244502 | 10/1986 |
| JP | 61-246002 | 11/1986 |
| JP | S61-246002 | 11/1986 |
| JP | S62-39201 | 2/1987 |
| JP | S62-11610 | 5/1987 |
| JP | S62-116102 | 5/1987 |
| JP | 10-26401 | 1/1989 |
| JP | 8-183010 | 7/1996 |
| JP | 10-272610 | 10/1998 |
| JP | 2000-102907 | 4/2000 |
| JP | 2000141316 | 5/2000 |
| JP | 2001-121512 | 8/2001 |
| NZ | 225428 | 3/1991 |
| NZ | 280716 | 2/1999 |
| NZ | 304884 | 3/1999 |
| RU | 642166 | 1/1979 |
| SE | 379 167 | 9/1975 |
| SE | 379167 | 9/1975 |
| WO | 85/00040 | 1/1985 |
| WO | 85/0040 | 1/1985 |

(56) References Cited

FOREIGN PATENT DOCUMENTS

| WO | 92/19429 | 11/1992 |
|---|---|---|
| WO | 95/27600 | 10/1995 |
| WO | 9955505 | 11/1999 |
| WO | 00/05955 | 2/2000 |
| WO | WO 0005955 A1 * | 2/2000 |
| WO | 00/24259 | 5/2000 |
| WO | 00/24528 | 5/2000 |
| WO | 00/78281 | 12/2000 |
| WO | 01/91925 | 12/2001 |
| WO | 01/91925 A | 12/2001 |
| WO | 02/06417 | 1/2002 |
| WO | WO 0206417 A1 * | 1/2002 |
| WO | 03/103392 | 12/2003 |
| WO | 2004/091875 | 10/2004 |
| WO | 2006044218 | 4/2006 |

OTHER PUBLICATIONS

American Wood-Preservers' Association Standard E10-01 (2003), pp. 1-11.*
American Wood-Preservers' Association Standard E11-97 (2003), pp. 1-3.*
Davis, Food Storage and Preservative-treated Wood, Alaska Science Forum (Mar. 10, 1980) [online], [retrieved on Nov. 10, 2008]. Retrieved from the Internet <URL:http://www.gi.alaska.edu/ScienceForum/ASF3/380.html>.*
STN online, file SCISEARCH, Acc. No. 1993:540390 (Siegfried, Comparative Toxicity of Pyrethroid Insecticides to Terrestrial and Aquatic Insects, Environmental Toxicology and Chemistry (1993), vol. 12, No. 9, pp. 1683-1689), Abstract.*
Koch, Synthesis of nanostructured materials by mechanical milling: problems and opportunities, NanoStructured Materials (1997), vol. 9, pp. 12-22.*
The Merck Index (12th ed. 1996), pp. 1555, 1556.*
English language translation of JP 2000141316, Schreiber Translations, Inc. (2009), pp. 1-26.*
Superior Court of New Jersey, Decision After Trial, *Phibro-Tech, Inc. v. Osmose Holding, Inc*. Jun. 25, 2007.
Liu, Y. et al.; "Use of Nanoparticles for the Controlled Release of Biocides in Pressure-Treated Solid Wood"; Polymer Preprints 38(2), 1997, pp. 624-625.
Liu, Y. et al.; Michigan Technical Univ., Dept of Chemistry, Houghton, MI; "Use of Polymeric Nanoparticles for Controlled Release of Biocides in Solid Wood"; Materials Research Symposium Proceedings Series; 1998; vol. 550, Abstract GG3.4.
Liu, Y.; "Use of Polymer Nanoparticles as Carriers for the Controlled release of Biocides in Solid Wood"; Ph. D. Dissertation of Yong Liu; Michigan Technological University, Houghton, MI, 1999.
Liu, Y. et al.; "Use of Nanoparticles for Controlled Release of Biocides in Solid Wood"; Journal of Applied Polymer Science, vol. 79, 2001, pp. 458-465.
Lide; "Characteristics of Particles and Particle Dispersoids"; Handbook of Chemistry and Physics; 75th Edition; 1994; Florida: CRC Press, pp. 15-38. .
Shaw; www.fda.gov/ohrms/dockets/ac/01/slides/3763s2_09_shaw.ppt; 2001.
International Society of Soil Science. (http://www.clays.org.au/mins.htm) (2006).
Hawley's Condensed Chemical Dictionary, 14th edition; John Wiley & Sons, Inc., 2001, p. 86.
Backman P. A. et al., The Effects of Particle Size and Distribution on Performance of the Fungicide Chlorothalonil, Phytopathology, St. Paul, MN, US, vol. 66, No. 10, 1 Jan. 1, 1976, pp. 1242-1245, XP009062911.
Koch, C.C., Synthesis of Nanostructured Materials by Mechanical Milling: Problems and Opportunities, NanoStructured Materials, vol. 9, pp. 13-22, 1997.
AWPA Standard E7-01, 2006.
AWPA Standard E10-1, 2005.
The Merck Index (12th Ed. 1996) Merck & Co., Inc., pp. 1555-1556.
Davis, Food Storage and Preservative-Treated Wood, Alaska Science Forum (Mar. 10, 1980) [online] [retrieve on Nov. 10, 2008]. URL:http://www.gi.alaska.edu/Science Forum/ASF3/380.htm/.
Schultz, T. P., et al., A Brief Overview of Non-Arsenical Wood Preservative, American Chemical Society, Chapter 26, pp. 420-429, 2003.
S. E. A. McCallan, The Nature of the Fungicidal Action of Copper and Sulfur, The Botinical Review, pp. 629-643, Aug. 30, 1948.
M. Humar et al., Influence of Moisture Content on EPR Parameters of Copper in Impregnated Wood, Holz als Roh-und Werkstoff 59 (2001) 254-255.
M. Humar et al., Changes of the pH of Impregnated Wood During Exposure to Wood-Rotting Fungi, Holz als Roh- und Werkstoff 59 (2001) 288-293.
A. Pizzi, A New Approach to Non-Toxic, Wide-Spectrum, Ground-Contact Wood Preservatives. Part I. Approach and Reaction Mechanisms, Holzforschung 47 (1993) 253-260.
A. Pizzi, A New Approach to Non-Toxic, Wide Spectrum, Ground-Contact Wood Preservatives. Pat II. Accelerated and Long-Term Field Tests, Holzforschung 47 (1993) 343-348.
Stan Lebow, et al., Fixation Effects on the Release of Copper, Chromium and Arsenic From CCA-C Treated Marine Piles, Report Prepared for American Wood-Preservers' Association Subcommittee P-3, Piles, Aug. 1999, pp. 168-174.
Izabela Ratajczak, et al., Fixation of Copper(II)-Protein Formulation in Wood: Part 1. Influence of Tannic Acid on Fixation of Copper in Wood, Holzforschung, vol. 62, pp. 294-299, 2008.
S. N. Kartal, et al., Do the Unique Properties of Nanometals Affect Leachability or Efficacy Against Fungi and Termines?, International Biodeterioration & Biodegradation 63 (2009) 490-495.
H. Kubel, et al., The Chemistry and Kinetic Behaviour of Cu-Cr-As/B Wood Preservatives—Part 5. Reactions of CCB and Cellulose, Lignin and their Simple Model Compounds, Holzforschung und Holzverwertung 34 (1982) 4, pp. 75-83.
A. Pizzi, et al., The Chemistry and Kinetic Behaviour of Cu-Cr-AS/B Wood Preservatives—Pat 6. Fixation of CCB in Wood and Physical and Chemical Comparison of CCB and CCA, Holzforschung and Holzverwertung 34 (1982) 5, pp. 80-86.
Raul A. Wapnir, Copper Absorption and Bioavailability, Am J Clin Nutr 1998; 67(suppl.): 1054S-60S.
Gadi Borkow, et al., Copper As A Biocidal Tool, Proceedings, Ninety-Fifth Annual Meeting of the American Wood-Preservers' Association, vol. 95, May 16-19, 1999.
H. S. Rathore, et al., Fungicide and Herbicide Residues in Water, Handbook of Water Analysis, pp. 608-654, Handbook of Water Analysis, 2000.
T.C. Crusberg, et al., Biomineralization of Heavy Metals, pp. 409-417, 2004.
R. Thompson, CBE, The Chemistry of Wood Preservation, Feb. 28-Mar. 1, 1991.
H. M. Barnes, et al., The Impact of Test Site and Oil Content on the Performance of Pentachlorophenol-treated Wood, Forest Products Journal, vol. 56, No. 5, pp. 43-47, May 2006.
J.J. Morrell, Wood Pole Maintenance Manual (1996 Edition), Research Contribution Oct. 15, 1996, p. 22.
Helmuth Rech, Location of Pentachlorophenol by Electron Microscopy and Other Techniques In Cellon Treated Douglas-Fir, Forest Products J. 21/1, pp. 38-43, Jan. 1971.
M. Humar, et a., Effect of Oxalix, Acetic Acid, and Ammonia on Leaching of Cr and Cu from Preserved Wood, Wood Sci Technol 37 (2004) 463-473.
Liu, Y. et al., Use of Nanoparticles for the Controlled Release of Biocides in Pressure-Treated Solid Wood, Polymer Preprints 38(2), 1997, pp. 624-625.
Liu, Y., Use of Polymer Nanoparticles as Carriers for the Controlled Release of Biocides in Solid Wood, Ph. D. Dissertation of Young, Liu; Michigan Technological University, Houghton, MI, 1999.
Liu, Y., Use of Nanoparticles for Controlled Release of Biocides in Solid Wood, Journal of Applied Polymer Science, vol. 79, 2001, pp. 458-465.
LIDE, Characteristics of Particles and Particle Dispersoids, Handbook of Chemistry and Physics, 75th Edition, 1994; Florida, CRC Press, pp. 15-38.

(56) References Cited

OTHER PUBLICATIONS

Shaw: www.fda,gov/ohrms/dockets/ac/01/slides/3763s2_09_shaw:ppt; 2001.

International Society of Soil Science, (http:/www.clays.org.au/mins.htm), (2006).

Hawleys Condensed Chemical Dictionary, 14th Edition, John Wiley & Sons, Inc., 2001, p. 86.

5.1 Inorganic Fungicides—5.1.1 Metal Salts, Pesticide Chemistry, pp. 272-486, 1988.

"A New Approach to Non-Toxic, Wide-Spectrum, Ground-Contact Wood Preservatives, Part I. Approach And Reaction Mechanisms," Holzforschung vol. 47, No. 3, pp. 253-260, 1993.

American Wood Preservers' Association (AWPA) Standard E10-1, 2005.

American Wood Preservers' Association (AWPA) Standard E7-01, 2006.

American Wood Preservers' Association (AWPA) Standard E-11-06, pp. 1-3, 2006, replaces AWPA Standard E-11-97, pp. 1-3, 2003.

Backman, P.A. et al., The Effects of Particle Size and Distribution on Performance of the Fungicide Chlorothalonil, Phytopathology, St. Paul, MN, US, vol. 66, No. 10, 1 Jan. 1, 1976, pp. 1242-1245, XP009062911.

Barnes, H. M., et al., The Impact of Test Site and Oil Content on the Performance of Pentachlorophenol-treated Wood, Forest Products Journal, vol. 56, No. 5, pp. 43-47, May 2006.

Borkow, Gadi, et al., Copper As A Biocidal Tool, Proceedings, Ninety-Fifth Annual Meeting of the American Wood-Preservers' Association, vol. 95, May 16-19, 1999.

Crusberg, T.C., et al., Biomineralization of Heavy Metals, pp. 409-417, 2004.

Cui, F. and Archer, K. J., "Treatment of lumbar with preservative/water repellent emulsions—The significance of shear stability on penetration," The International Research Group on Wood Preservation, IRG/WP 97-20124, Paper prepared for the 28th Annual Meeting, Whistler, British Columbia, Canada (May 25-30, 1997).

Davis, Food Storage and Preservative-Treated Wood, Alaska Science Forum (Mar. 10, 1980) [online] [retrieve on Nov. 10, 2008]. URL: http://www.gi.alaska.edu/Science Forum/ASF3/380.htm/.

Feist and Mraz, Forest Products Lab Madison Wis., Wood Finishing: Water Repellents and Water-Repellent Preservatives. Revision, Report Number-FSRN-FPL-0124-Rev (NTIS 1978).

Fojutowski, A.; Lewandowski, O., Zesz. Probl. Postepow Nauk Roln. No. 209: 197-204 (1978).

Hamilton, R. L. and Cosse, O. K., "Thermal Conductivity of Heterogenous Two-Component Systems," Ind. & Engr. Chem. Fund., 1, 187-191 (1962).

Hawley's Condensed Chemical Dictionary, 14th edition; John Wiley & Sons, Inc., p. 86 (2001).

Humar, M., et al., Changes of the pH of Impregnated Wood During Exposure to Wood-Rotting Fungi, Holz als Roh-und Werkstoff 59 pp. 288-293 (2001).

Humar, M., et al., Effect of Oxalix, Acetic Acid, and Ammonia on Leaching of Cr and Cu from Preserved Wood, Wood Sci Technol 37, pp. 463-473 (2004).

Humar, M., et al., Influence of Moisture Content on EPR Parameters of Copper in Impregnated Wood, Holz als Roh-und Werkstoff 59, pp. 254-255 (2001).

International Society of Soil Science. (http://www.clays.org.au/mins.htm).

Kartal, S. N., et al., Do the Unique Properties of Nanometals Affect Leachability or Efficacy Against Fungi and Termines? International Biodeterioration & Biodegradation 63 pp. 490-495 (2009).

Koch, C. C., Synthesis of Nanostructured Materials by Mechanical Milling: Problems and Opportunities, NanoStructured Materials, vol. 9, pp. 13-22 (1997).

Kubel, H., et al., The Chemistry and Kinetic Behaviour of Cu-Cr-As/B Wood Preservatives—Part 5. Reactions of CCB and Cellulose, Lignin and their Simple Model Compounds, Holzforschung und Holzverwertung 34 (1982) 4, pp. 75-83.

Laks, et al., "Polymer Nanoparticles as a Carrier System for Wood Preservatives," PowerPoint Presentation to Rohm & Haas under confidentiality agreement, Oct. 30, 1998 (even-numbered pages not available).

Lebow, Stan, et al., Fixation Effects on the Release of Copper, Chromium and Arsenic From CCA-C Treated Marine Piles, Report Prepared for American Wood-Preservers' Association Subcommittee P-3, Piles, pp. 168-174, Aug. 1999.

Lide; "Characteristics of Particles and Particle Dispersoids"; Handbook of Chemistry and Physics; 75th Edition; 1994; Florida: CRC Press, pp. 15-38.

Liu, Y., et al., "Use of Nanoparticles for the Controlled Release of Biocides in Pressure-Treated Solid Wood"; Presentation at American Chemical Society, Las Vegas, Oct. 1997.

Liu, Y., et al.; "Use of Nanoparticles for Controlled Release of Biocides in Solid Wood"; Journal of Applied Polymer Science, vol. 29, pp. 458-465 (2001).

Liu, Y., et al.; Michigan Technical Univ., Dept. of Chemistry, Houghton, MI; "Use of Polymeric Nanoparticles for Controlled Release of Biocides in Solid Wood"; Materials Research Society Symposium Proceedings Series; vol. 550, Abstract GG3.4 (1998).

Liu, Y., et al; "Use of Nanoparticles for the Controlled Release of Biocides in Pressure-Treated Solid Wood"; Polymer Preprints 38(2), pp. 624-625 (1997).

Liu, Y.; "Use of Polymer Nanoparticles as Carriers for the Controlled release of Biocides in Solid Wood"; Ph.D. Dissertation of Yong Liu; Michigan Technological University, Houghton, MI, 1999.

Morrell, J. J. Wood Pole Maintenance Manual (1996 Edition), Research Contribution 15, p. 22, Oct. 1996.

Nanotechnology in brief, Feb. 20, 2004, available at http://nanotechweb.org/articles/news/3/2/12/1.

Nasibulin, Albert G., Ahonen, P. Petri, Richard, Richard, Olivier, Esko I, "Copper and Copper Oxide Nanoparticle Formation by Chemical Vapor Nucleation From Copper (II) Acetylacetonate," Journal of Nanoparticle Research 3(5-6): 383-398 (2001).

Panshin AJ and De Zeeuw, Carl, Textbook of Wood Technology, 4th ed. pp. 112-113 (1980).

Pizzi, A., A New Approach to Non-Toxic, Wide Spectrum, Ground-Contact Wood Preservatives. Part II. Accelerated and Long-Term Field Tests, Holzforschung 47 pp. 343-348 (1993).

Pizzi, A., et al., The Chemistry and Kinetic Behaviour of Cu-Cr-As/B Wood Preservatives—Part 6. Fixation of CCB in Wood and Physical and Chemical Comparison of CCB and CCA, Holzforschung and Holzverwertung 34 5, pp. 80-86 (1982).

Ratajczak, Izabela, et al., Fixation of Copper(II)-Protein Formulation in Wood: Part 1. Influence of Tannic Acid on Fixation of Copper in Wood, Holzforschung, vol. 62, pp. 294-299 (2008).

Rathore, H. S., et al., Fungicide and Herbicide Residues in Water, Handbook of Water Analysis, pp. 608-654 (2000).

Rech, Helmuth, Location of Pentachlorophenol by Electron Microscopy and Other Techniques in Cellon Treated Douglas-Fir, Forest Products J. 21/1, pp. 38-43, Jan. 1971.

S. E. A. McCallan, The Nature of the Fungicidal Action of Copper and Sulfur, The Botanical Review.

Schultz, T .P., et al., A Brief Overview of Non-Arsenical Wood Preservative, American Chemical Society, Chapter 26, pp. 420-429 (2003).

Shaw; www.fda.gov/ohrms/dockets/ac/011slides/3763s2_09_shaw.ppt; 2001.

STN online, file SCISEARCH, Acc. No. 1993:540390 (Siegfried, Comparative Toxicity of Pyrethroid Insecticides to Terrestial and Aquatic Insects, Environmental Toxicology and Chemistry, vol. 12, No. 9, pp. 1683-1689, Abstract (1993).

Superior Court of New Jersey Chancery Division, Final Judgment, *Phibro-Tech, Inc.* v. *Osmose Holdings, Inc.*, Osmose, Inc., Aug. 14, 2007.

Superior Court of New Jersey, Decision After Trial, *Phibro-Tech, Inc.* v. *Osmose Holding, Inc.*, Jun. 25, 2007.

Supplementary European Search Report for PCT/US2005/016503 dated Feb. 2, 2009.

Supplementary European Search Report for PCT/US2005/037303 dated Feb. 5, 2009.

(56) References Cited

OTHER PUBLICATIONS

Wapnir, Raul A., Copper Absorption and Bioavailability, Am J Clin Nutr 1998; 67 (suppl.): 1054S-60S.

The Merck Index (12th Ed.) Merck & Co., Inc., pp. 1555-1556 (1996).

Thompson, R., CBE, The Chemistry of Wood Preservation, Feb. 28-Mar. 1, 1991.

The Copper Champs! Unique Copper Hydroxide Formulations (Brochure), Nufarm Americas Inc. (2002).

Zahora, A. R. and Rector, C.M., "Water Repellent Additives for Pressure Treatments" Proceedings of the Eleventh Annual Meeting of the Canadian Wood Preservation Association, Toronto, Ontario, 11:22-41 (Nov. 6 and 7, 1990).

"Defendants' Answer to Plaintiffs Amended Complaint and Defendants' Counterclaims," *Osmose, Inc.* v. *Arch Chemicals, et al.*, USDC, Eastern District of VA, Norfolk Division Case No. C.A. No. 2:10 cv 108-JBF/FBS.

"Osmose's Answer to Defendants' Counterclaims," *Osmose, Inc.* v. *Arch Chemicals, et al.*, USDC, Eastern District of VA, Norfolk Division Case No. C.A. No. 2:10 cv 108-JBF/FBS.

Amended Notice of Opposition to Grant of Patent (Section 21) and Statement of Case (Application No. 542889) filed by Mattersmiths Holdings Limited on Aug. 23, 2010; and Notice of Opposition to Grant of Patent (Section 21) (Application No. 542889) filed by Mattersmiths Holdings Limited on Jun. 22, 2010.

Notice of Opposition to a European Patent (Application No. EP04776802.3/Patent No. EP1651401), filed by Dr. David Elsy on Apr. 21, 2010.

Statement of Grounds and Particulars filed by Arch Wood Protection Pty Ltd. with the Commissioner of Patents on Dec. 18, 2009, In the Matter of Australian Patent Application No. 2004230950 in the name of Osmose, Inc.

Rudd, et al. "The Influence of Ultraviolet Illumination on the Passive Behavior of Zinc," Journal of the Electrochemical Society, 147 (4) pp. 1401-1407, 2000.

American Wood-Preservers' Association (AWPA) Standard A3-00, 2003.

Bailey, Irving W., "The Preservative Treatment of Wood, II. The Structure of the Pit Membranes in the Tracheids of Conifers and their Relation to the Penetration of Gases, Liquids, and Finely Divided Solids into Green and Seasoned Wood," Forestry Quarterly, 11:12-20, p. 15 (1913).

Request for Inter Partes Reexamination of U.S. Patent No. 7,674,481 filed with the United States Patent and Trademark Office by Arch Wood Protection, Inc. on Aug. 13, 2010 and a draft of the Request.

Merriam-Webster's Collegiate Dictionary, 10th ed., 1993.

Proceedings of the Fourth International Congress of Pesticide Chemistry (IUPAC), Article VII-23, 1978.

Supplementary European Search Report dated Apr. 21, 2009 for PCT/US2005/035946.

Statutory Declaration of Dr. Robin Nicholas Wakeling, in the matter of Australian Patent Acceptance No. 2004230950 and Opposition thereto, dated Sep. 20, 2010.

Hungarian Search Report dated Jul. 15, 2010 for Singaporean Patent Application No. 200717645-6.

Australian Patent Office Examination Report dated Jun. 1, 2010 for Singaporean Patent Application No. 200717652-2.

"Defendants' Supplemental Response to Interrogatory No. 12 and its Subparts," *Osmose, Inc.* v. *Arch Chemicals, et al.*, USDC Eastern District of VA, Norfolk Division Case No. C.A. No. 2:10 cv 108-JBF, (2010).

"Fungicides, Biocides and Preservatives for Industrial and Agricultural Applications," by Ernest W. Flick, 1987, Noyes Publications, p. 184.

Opinion and Order, *Osmose, Inc.* v. *Arch Chemicals, Inc.*, et al., Jan. 28, 2011, USDC Eastern District of Virginia, Norfolk Division, Civil Action No. 2:10 cv 108.

Expert Report of Dr. Frank Beall, Ph.D. Concerning the Invalidity of U.S. Patent No. 7,674,481, USDC Eastern District of Virginia, Norfolk Division, Civil Action No. 2:10cv108, Jan. 21, 2011.

Supplemental Expert Report of Dr. Frank Beall, Ph.D. Concerning the Invalidity of U.S. Patent No. 7,674,481, Feb. 11, 2011, USDC Eastern District of Virginia, Norfolk Division, Civil Action No. 2:10cv108.

Rebuttal Expert Report of John Ruddick, USDC Eastern District of Virginia, Norfolk Division, Civil Action No. 2:10cv108, Feb. 22, 2011 (redacted).

American Wood Preservers' Association (AWPA) Standard E10-06, "Standard Method of Testing Wood Preservatives by Laboratory Soil-Block Cultures," 2007.

American Wood Preservers' Association (AWPA) Standard E10-09, "Standard Method of Testing Wood Preservatives by Laboratory Soil-Block Cultures," 2010.

American Wood Preservers' Association (AWPA) Standard E11-06, "Standard Method of Determining the Leachability of Wood Preservatives," 2007.

American Wood Preservers' Association (AWPA) Standard E22-09, "Standard Accelerated Laboratory Method for Testing the Efficacy of Preservatives Against Wood Decay Fungi Using Compression Strength," 2010.

ASTM D5664, "Standard Test Method for Evaluating the Effects of Fire-Retardant Treatments and Elevated Temperatures on Strength Properties of Fire Retardant Treated Lumber," 2002.

"Preservation of Timber with Zinc Chloride by the Steeping Process," Technical Notes, Forest Products Laboratory, U.S. Forest Service, (1919).

Freeman, Mike H., et al., "A Comprehensive Review of Copper-Based Wood Preservatives," Forest Products Journal, vol. 58, No. 11, pp. 6-27, Nov. 2008.

Stirling, Rod, et al., "Micro-Distribution of Micronized Copper in Southern Pine," The International Research Group on Wood Protection, 39th Annual Meeting, May 25-28, 2008.

The Federal Circuit Bar Association Model Patent Jury Instructions, last edited Feb. 18, 2010.

Liese, W., "Fine Structure of Bordered Pits in Softwoods," Cellular Ultrastructure of Woody Plants, pp. 271-290, 1965.

Graph, "Fine Structure of Bordered Pits in Softwoods", (1965).

Response to Office Action by Patent Owner in Inter Partes Reexamination under 37 CFR § 1.945, USPTO Reexamination Control No. 95/001,418, filed by Osmose, Inc., Dec. 21, 2010.

Third Party Comments After Patent Owner Response, USPTO Reexamination Control No. 95/001,418, filed by Arch Wood Protection, Inc., Jan. 20, 2011.

Patent Owner's Response Under 37 CFR 1.951(a) to the Action Closing Prosecution in Inter Partes Reexamination Control No. 95/001,418. May 27, 2011.

Declaration of Dr. John N.R. Ruddick Under 37 CFR 1.132, in Inter Partes Reexamination Control No. 95/001,418. May 26, 2011.

Decision on Appeal in Reexamination Control No. 95/001,418, Patent Trial and Appeal Board, Jan. 28, 2013.

\* cited by examiner

Coniferous Wood Anatomy

BORDERED PIT

Cross section of micronized copper hydroxide treated wood sprayed with copper indicator Cross section of untreated wood sprayed with copper indicator

MICRONIZED WOOD PRESERVATIVE FORMULATIONS

This application claims priority to U.S. Provisional application no. 60/568,485 filed on May 6, 2004, the disclosure of which is incorporated herein by reference. This application is also a continuation-in-part of U.S. Non-provisional application Ser. No. 10/821,326 filed on Apr. 9, 2004, which in turn claims priority to U.S. Provisional Application No. 60/461,547, filed Apr. 9, 2003, and U.S. Provisional Application No. 60/518,994, filed Nov. 11, 2003, the disclosures of which are incorporated herein by reference.

FIELD OF THE INVENTION

The present invention is related generally to the field of wood preservatives and more particularly to a wood preservative composition comprising micronized particles.

BACKGROUND OF THE INVENTION

Wood preserving compositions are well known for preserving wood and other cellulose-based materials, such as paper, particleboard, textiles, rope, etc., against organisms responsible for the destruction of wood, including fungi and insects. Many conventional wood preserving compositions contain copper amine complexes. Copper amine complexes have been used in the past because the amine solubilizes the copper in aqueous solutions. The copper in such copper amine complexes is obtained from a variety of copper bearing materials, such as copper scrap, cuprous oxide, copper carbonate, copper hydroxide, a variety of cuprous and cupric salts, and copper bearing ores. The amine in such copper amine complexes is normally obtained from an aqueous solution of ammonia and ammonium salts, such as ammonium carbonate, and ammonium sulfate, ethanolamines, etc. For example, U.S. Pat. No. 4,622,248 describes forming copper amine complexes by dissolving copper (II) oxide [CuO] (also known as cupric oxide) in ammonia in the presence of ammonium bicarbonate.

The disadvantage of using ammonia as a copper solubilizing agent lies in the strong odor of ammonia. Additionally, copper ammonia preservatives can affect the appearance of the treated wood giving surface residues an undesirable color. In recent years, many amine-containing compounds, such as the ethanolamines and aliphatic polyamines, have been used to replace ammonia to formulate water-soluble copper solutions. These compounds were chosen because of their strong complexing ability with copper and because they are essentially odorless. U.S. Pat. No. 4,622,248 discloses a method of preparing copper amine complexes by dissolving a mixture of copper (II) carbonate [$CuCO_3$] and copper (II) hydroxide [$Cu(OH)_2$] in ethanolamine and water. The complexing amine (i.e., the ligand) and copper (II) ion combine stoichiometrically and thus the weight ratio of reagents will be different for each complexing amine. However, copper amine based preservatives have higher copper loss due to leaching as compared to traditional copper based preservatives such as chromated copper arsenate (CCA).

In addition to metal biocides, existing wood preservatives can also contain organic biocides. However, many organic biocides currently in use are not water soluble. Therefore, solubilizing agents, surfactants and wetting agents are often added to either solubilize or form emulsions of the organic biocide to formulate a product that is suitable for the treatment of wood or other cellulose substrates.

However, the solubilizing agents, surfactants, and wetting agents are costly and the use of these products may result in enhanced leaching of the biocides when the treated material comes into contact with moisture. Such enhanced leaching is considered to be the result of the solubilizing agents, surfactants and wetting agents which remain in the wood after treatment. Because these compounds continue to cause leaching of the metal and/or biocide from the treated wood, field performance problems or environmental issues can result.

Despite many efforts to address these deficiencies in existing wood preservatives, there has been an unmet need to produce aqueous metal-based preservatives that are suitable for treating wood and other cellulose-based materials while minimizing the undesirable leaching of metal ions and/or biocide from treated materials when exposed to water. This need is met by the invention disclosed herein.

SUMMARY OF THE INVENTION

The present invention provides micronized compositions for preservation of wood. In one embodiment, the compositions comprise metal or metal compounds as micronized particles.

In another embodiment, the compositions comprise metal or metal compounds and organic biocides. The metal is in an insoluble (micronized) form. The metal compounds may be in a soluble form or in a water insoluble (micronized) form. The organic biocides may be soluble or water insoluble (micronized). In the compositions of this embodiment, at least one component (either a metal/metal compound or a biocide) is micronized.

Accordingly, in one embodiment is provided a wood preservative composition comprising micronized metal, metal compounds or combinations thereof.

In another embodiment is provided a wood preservative composition comprising a micronized metal or metal compound and a soluble organic biocide.

In another embodiment is provided a wood preservative composition comprising micronized metal/metal compounds and micronized organic biocides.

In another embodiment is provided a composition comprising soluble metal compound and micronized organic biocides.

Also provided is a method for using the compositions of the present invention. The method comprises the step of contacting a cellulosic material, such as wood, with a composition of the present invention. When the compositions of the present invention are used for preservation of wood, there is minimal leaching of the metal or metal and the biocide from wood.

In one embodiment, the preferred metal for wood preserving type applications is copper in the form of a copper compound having a particle size 0.001 microns to 25.0 microns. The copper compound can optionally be mixed with a variety of water soluble and/or water insoluble biocides and then vacuum impregnated, vacuum/pressure or dip impregnated into cellulosic material by standard methods to effectively preserve the material from agents that degrade cellulosic material such as fungi, insects, bacteria etc.

BRIEF DESCRIPTION OF THE FIGURES

The patent or application filed contains at least one drawing executed in color. Copies of this patent or patent application publication with color drawing(s) will be provided by the Office upon request and payment of the necessary fee.

micronized copper hydroxide at copper retentions of 0.1 pounds per cubic foot (pcf) and 0.2 pcf according to American Wood Preservers' Association (AWPA) Standard E11-97 "Standard Method of Determining the Leachability of Wood Preservatives".

Figure 1A:
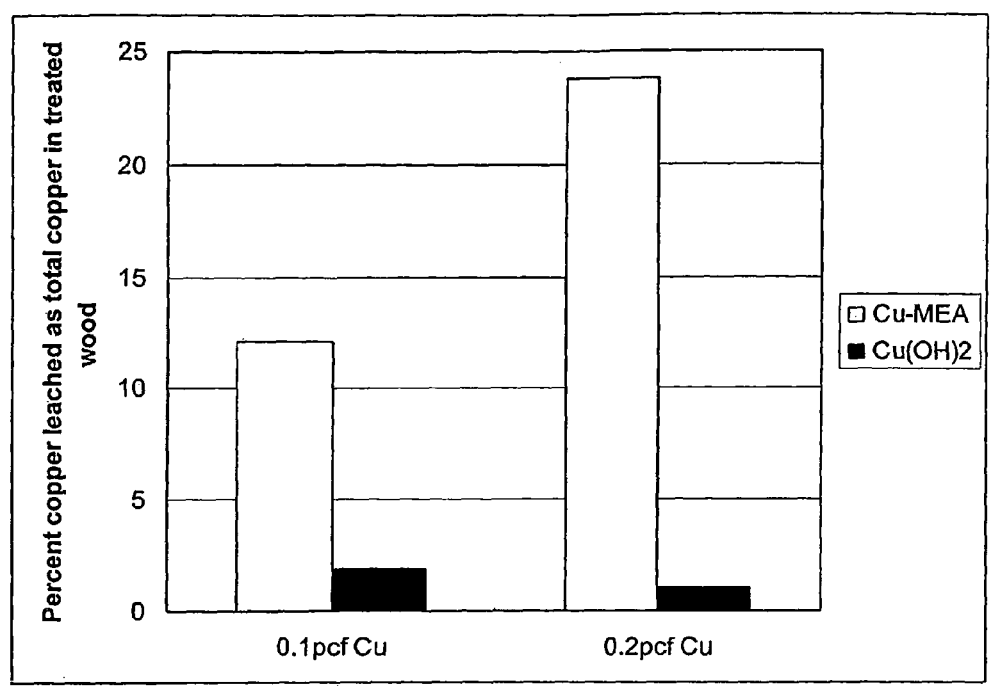
FIG. 1A is a comparison of copper leaching from wood treated with copper monoethanolamine (copper mea) vs.
Figure 1B:
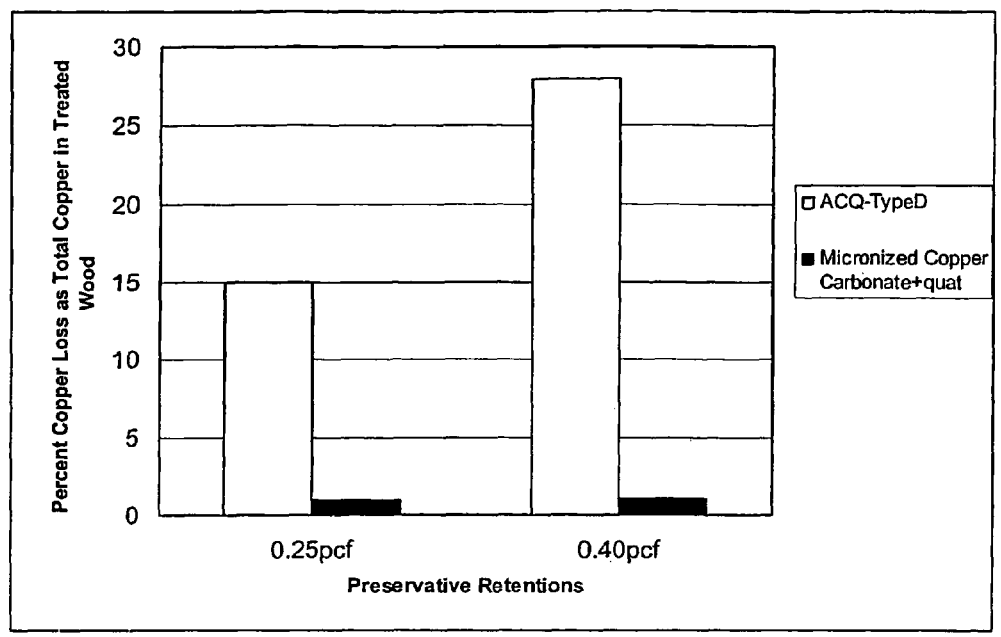

FIG. 1B is a comparison of copper leaching from wood treated with a commercial copper based formulation ACQ-Type D and micronized copper carbonate plus dimethyldidecylammonium carbonate/bicarbonate (quat) at preservative retentions of 0.25 pcf and 0.40 pcf. The leaching test was conducted following the procedure described in AWPA Standard E11-97 "Standard Method of Determining the Leachability of Wood Preservatives".

Figure 2:
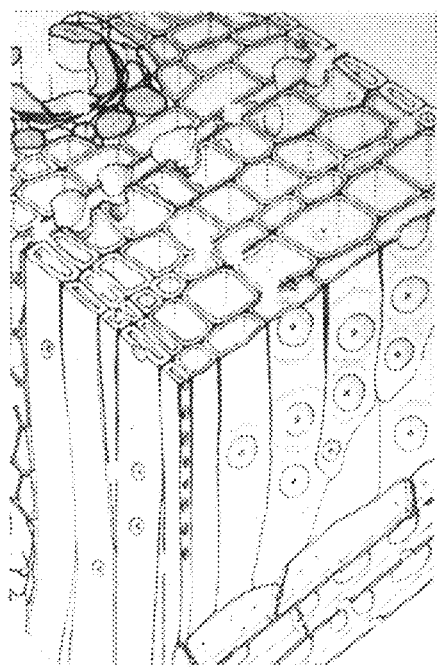

FIG. 2 depicts the anatomy of coniferous wood.

Figure 3:
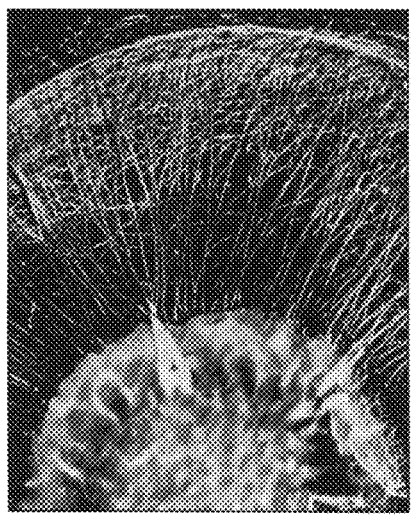
Figure 3:

FIG. 3 depicts the border pit structure for coniferous wood.

Figure 4A:
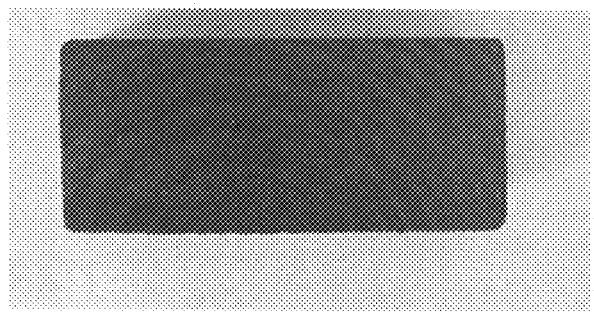
Figure 4A:
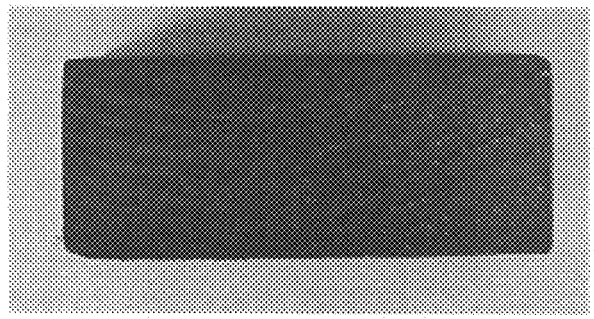

FIG. 4A depicts the uniform copper penetration in wood treated with micronized copper hydroxide according to AWPA Standard A3-00 "Standard Method for Determining Penetration of Preservatives and Fire Retardants".

Figure 4B:
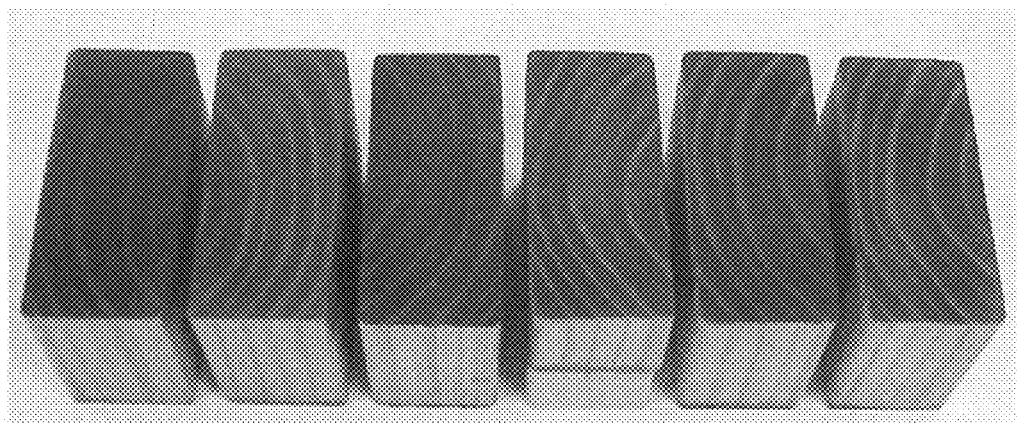

FIG. 4B depicts the uniform copper penetration in wood treated with micronized copper carbonate plus quat. The determination of copper penetration was conducted following the procedures described in AWPA Standard A3-00 "Standard Method for Determining Penetration of Preservatives and Fire Retardants".

Figure 5:
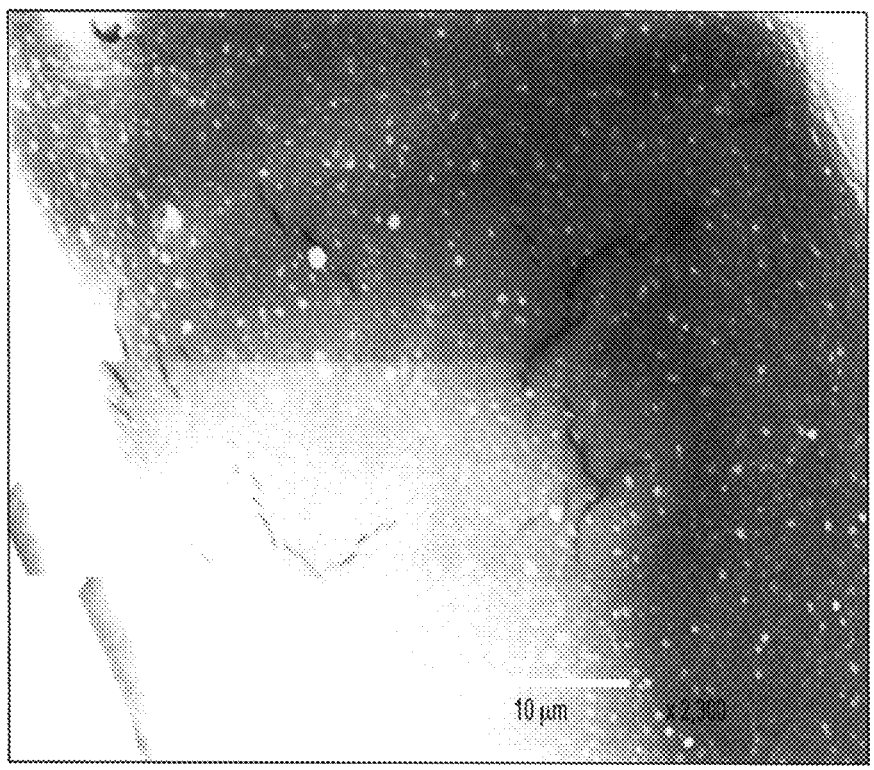

FIG. 5 depicts the uniform particle distribution of cupric oxide through the cells of the wood treated with micronized CuO.

Figure 6:
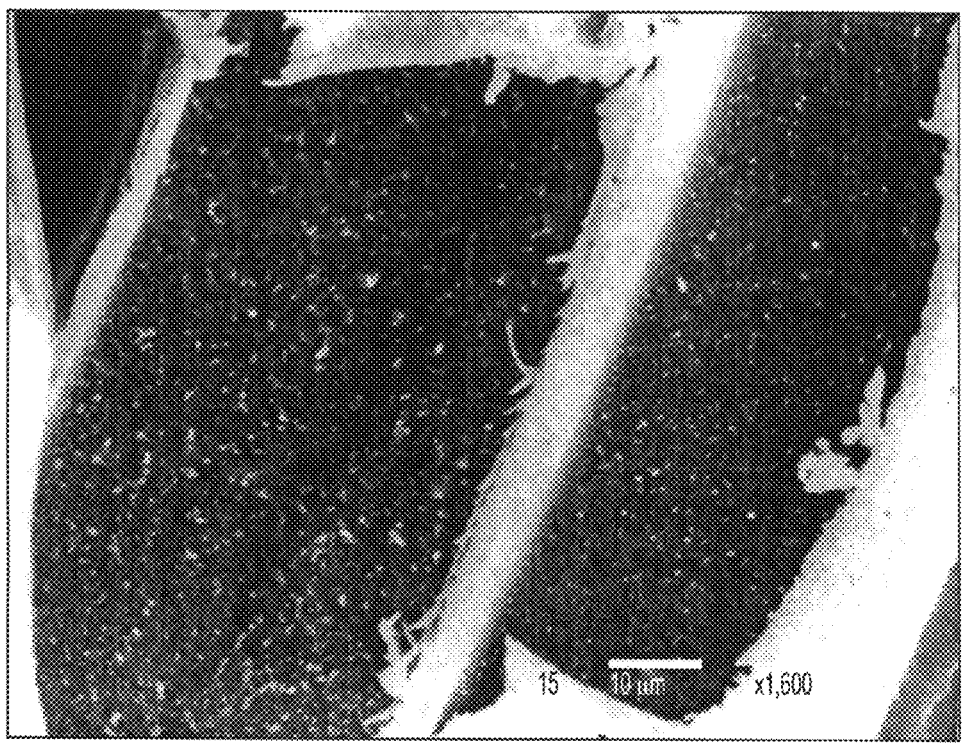

FIG. 6 depicts a scanning Electron Micrograph of a Southern Pine wood treated with a micronized copper carbonate dispersion showing two views at magnification of 1600×.

DETAILED DESCRIPTION OF THE INVENTION

Unless stated otherwise, such as in the examples, all amounts and numbers used in this specification are intended to be interpreted as modified by the term "about". Likewise, all elements or compounds identified in this specification, unless stated otherwise, are intended to be non-limiting and representative of other elements or compounds generally considered by those skilled in the art as being within the same family of elements or compounds. The term "micronized" as used herein means a particle size in the range of 0.001 to 25 microns. Furthermore, it should be understood that "micronized" does not refer only to particles which have been produced by the finely dividing, such as by mechanical grinding, of materials which are in bulk or other form. Micronized particles can also be formed by other mechanical, chemical or physical methods, such as, for example, formation in solution, with or without a seeding agent, grinding or impinging jet. The term "preservative" as used herein means a composition that renders the material to which it is applied more resistant to insect, fungal or microbial attack than the same material without having the composition applied. The term "particle size" refers to the largest axis of the particle, and in the case of a generally spherical particle, the largest axis is the diameter.

The wood preservative compositions of the present invention comprise an inorganic component comprising a metal, metal compound or combinations thereof and optionally one or more organic biocides. Accordingly, the present invention provides micronized wood preservatives comprising one or more metal or metal compounds with or without one or more organic biocides. When the composition comprises both the metal/metal compounds and the organic biocides, the metal or metal compounds or the organic biocides are present as water insoluble micronized particles. In one embodiment, both the inorganic component and the organic biocide are present as micronized particles.

These compositions are used for treatment of cellulosic material such as wood. The leaching of metal from the treated wood is less for the present compositions than that observed from wood treated with non-micronized compositions.

A preferred metal is copper. Accordingly, in one embodiment, copper, copper compounds and/or copper complexes are used. The copper or copper compounds such as cuprous oxide (a source of copper (I) ions), cupric oxide (a source of copper (II) ions), copper hydroxide, copper carbonate, basic copper carbonate, copper oxychloride, copper 8-hydroxyquinolate, copper dimethyldithiocarbamate, copper omadine, copper borate, copper residues (copper metal byproducts) or any suitable copper source can be used as micronized particles having a particle size between 0.001 microns to 25 microns. These particles exhibit a relatively low solubility in water. Other metals, metal compounds or metal complexes as well as transition metals or transition metal compounds (including the lanthanide and actinide series elements) such as zinc, cadmium, silver, nickel, arsenic, bismuth, lead, chromium etc. can be used in place of copper, copper compounds or copper complexes.

The present invention includes any copper based compounds or copper complexes including chromated copper arsenates and other complexes. The present invention is not limited to ionically bound metals, and compounds in which the bonds to the metal are partially or totally covalent may be used.

The micronized particles can be obtained by wetting/dispersing and grinding copper compounds using a commercially available grinding mill or any other chemical, physical or mechanical means. Alternatively, the micronized copper compounds may also be purchased from commercial sources, which generally need to be ground further to be useful for wood preservation. For example, micronized copper hydroxide can be obtained from Phibro-Tech, Inc., Sumter, S.C. and ground further for use in the present invention. Micronized cupric oxide can also be obtained from Nanophase Technologies Corporation, Romeoville, Ill.

The copper source can be mixed with water with or without addition of a commercially available rheological additive such as a cellulosic derivative to form a finely dispersed suspension which can be mixed with a biocide to form a preservative system which is suitable to treat and protect wood from agents causing degradation. Other metals or metal compounds as well as transition metals or transition metal compounds (including the lanthanide and actinide series elements) such as tin, zinc, cadmium, silver, nickel, etc. and compounds thereof can be used in place of copper and copper compounds. The resulting metal dispersion or the metal biocide fluid dispersion are suitable for the preservation of wood and other cellulose-based materials.

The compositions of the present invention can be adjusted to the desired pH. For example, the pH can be adjusted to between 2 to 13 by the addition of acids or alkaline components. The acid or alkaline components can be added before, during or after preparation of the micronized particles.

The present invention includes the situation in which a water-soluble inorganic biocide is used in conjunction with a micronized organic biocide. A range of water-soluble inorganic biocides can be used. Included in this range are water-soluble compounds which could otherwise be used as micronized inorganic biocides in other embodiments of the present invention. Examples of such are water-soluble compounds in the list of copper compounds above. Other examples are compounds such as sodium fluoride, sodium borate, and boric acid. In general, the inorganic biocide has a solubility which is greater than 10 grams per liter.

The organic biocides useful in the present invention can be water soluble as well as water insoluble. Such organic biocides including fungicides, insecticides, moldicides, bactericides, algaecides etc. are well known to those skilled in the art and include azoles, quaternary ammonium compounds, borate compounds, fluoride compounds and combinations thereof.

Some non-limiting examples of water soluble biocides are quaternary ammonium compounds, such as alkyldimethylbenzylammonium chloride, dimethyldidecylammonium chloride, dimethyldidecylammonium carbonate/bicarbonate and the like.

Water insoluble organic biocides are also well known. Some non-limiting examples of water insoluble organic biocides are provided below.

Fungicides, insecticides and bactericides that can be used with the system are well known to those skilled in the art and include azoles, quaternary ammonium compounds, boron compounds, fluoride compounds disclosed herein and combinations thereof.

Quaternary ammonium compounds that can be mixed with micronized metal formulations have the following structures:

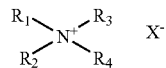

Where $R_1$, $R_2$, $R_3$, and $R_4$ are independently selected from alkyl or aryl groups and X-selected from chloride, bromide, iodide, carbonate, bicarbonate, borate, carboxylate, hydroxide, sulfate, acetate, laurate, or any other anionic group. Preferred quaternary ammonium compounds include alkyldimethylbenzylammonium chloride, alkyldimethylbenzylammonium carbonate/bicarbonate, dimethyldidecylammonium chloride, dimethyldidecylammonium carbonate/bicarbonate, etc.

Examples of fungicides which can be mixed with micronized metal formulations are provided in Table 1:

TABLE 1

| Aliphatic Nitrogen Fungicides |
| --- |
| butylamine; cymoxanil; dodicin; dodine; guazatine; iminoctadine |
| Amide Fungicides |
| carpropamid; chloraniformethan; cyazofamid; cyflufenamid; diclocymet; ethaboxam; fenoxanil; flumetover; furametpyr; prochloraz; quinazamid; silthiofam; triforine; benalaxyl; benalaxyl-M; furalaxyl; metalaxyl; metalaxyl-M; pefurazoate; benzohydroxamic acid; tioxymid; trichlamide; zarilamid; zoxamide; cyclafuramid; furmecyclox dichlofluanid; tolylfluanid; benthiavalicarb; iprovalicarb; benalaxyl; benalaxyl-M; boscalid; carboxin; fenhexamid; metalaxyl; metalaxyl-M; metsulfovax; ofurace; oxadixyl; oxycarboxin; pyracarbolid; thifluzamide; tiadinil; benodanil; flutolanil; mebenil; mepronil; salicylanilide; tecloftalam fenfuram; furalaxyl; furcarbanil; methfuroxam; flusulfamide |
| Antibiotic Fungicides |
| aureofungin; blasticidin-S; cycloheximide; griseofulvin; kasugamycin; natamycin; polyoxins; polyoxorim; streptomycin; validamycin; azoxystrobin; dimoxystrobin; fluoxastrobin; kresoxim-methyl; metominostrobin; orysastrobin; picoxystrobin; pyraclostrobin; trifloxystrobin |
| Aromatic Fungicides |
| biphenyl; chlorodinitronaphthalene; chloroneb; chlorothalonil; cresol; dicloran; hexachlorobenzene; pentachlorophenol; quintozene; sodium pentachlorophenoxide; tecnazene |
| Benzimidazole Fungicides |
| benomyl; carbendazim; chlorfenazole; cypendazole; debacarb; fuberidazole; mecarbinzid; rabenzazole; thiabendazole |
| Benzimidazole Precursor Fungicides |
| furophanate; thiophanate; thiophanate-methyl |
| Benzothiazole Fungicides |
| bentaluron; chlobenthiazone; TCMTB |
| Bridged Diphenyl Fungicides |
| bithionol; dichlorophen; diphenylamine |
| Carbamate Fungicides |
| benthiavalicarb; furophanate; iprovalicarb; propamocarb; thiophanate; thiophanate-methyl; benomyl; carbendazim; cypendazole; debacarb; mecarbinzid; diethofencarb, iodopropynyl butylcarbamate |
| Conazole Fungicides |
| climbazole; clotrimazole; imazalil; oxpoconazole; prochloraz; triflumizole; azaconazole; bromuconazole; cyproconazole; diclobutrazol; difenoconazole; diniconazole; diniconazole-M; epoxiconazole; etaconazole; fenbuconazole; fluquinconazole; flusilazole; flutriafol; furconazole; furconazole-cis hexaconazole; imibenconazole; ipconazole; metconazole; myclobutanil; penconazole; propiconazole; prothioconazole; quinconazole; simeconazole; tebuconazole; tetraconazole; triadimefon; triadimenol; triticonazole; uniconazole; uniconazole-P |

TABLE 1-continued

Dicarboximide Fungicides famoxadone; fluoroimide; chlozolinate; dichlozoline; iprodione; isovaledione; myclozolin; procymidone; vinclozolin; captafol; captan; ditalimfos; folpet; thiochlorfenphim Dinitrophenol Fungicides binapacryl; dinobuton; dinocap; dinocap-4; dinocap-6; dinocton; dinopenton; dinosulfon; dinoterbon; DNOC Dithiocarbamate Fungicides azithiram; carbamorph; cufraneb; cuprobam; disulfiram; ferbam; metam; nabam; tecoram; thiram; ziram; dazomet; etem; milneb; mancopper; mancozeb; maneb; metiram; polycarbamate; propineb; zineb Imidazole Fungicides cyazofamid; fenamidone; fenapanil; glyodin; iprodione; isovaledione; pefurazoate; triazoxide Morpholine Fungicides aldimorph; benzamorf; carbamorph; dimethomorph; dodemorph; fenpropimorph; flumorph; tridemorph Organophosphorus Fungicides ampropylfos; ditalimfos; edifenphos; fosetyl; hexylthiofos; iprobenfos; phosdiphen; pyrazophos; tolclofos-methyl; triamiphos Oxathiin Fungicides carboxin; oxycarboxin Oxazole Fungicides chlozolinate; dichlozoline; drazoxolon; famoxadone; hymexazol; metazoxolon; myclozolin; oxadixyl; vinclozolin Pyridine Fungicides boscalid; buthiobate; dipyrithione; fluazinam; pyridinitril; pyrifenox; pyroxychlor; pyroxyfur Pyrimidine Fungicides bupirimate; cyprodinil; diflumetorim; dimethirimol; ethirimol; fenarimol; ferimzone; mepanipyrim; nuarimol; pyrimethanil; triarimol Pyrrole Fungicides fenpiclonil; fludioxonil; fluoroimide Quinoline Fungicides ethoxyquin; halacrinate; 8-hydroxyquinoline sulfate; quinacetol; quinoxyfen Quinone Fungicides benquinox; chloranil; dichlone; dithianon Quinoxaline Fungicides chinomethionat; chlorquinox; thioquinox Thiazole Fungicides ethaboxam; etridiazole; metsulfovax; octhilinone; thiabendazole; thiadifluor; thifluzamide Thiocarbamate Fungicides methasulfocarb; prothiocarb Thiophene Fungicides ethaboxam; silthiofam Triazine Fungicides anilazine Triazole Fungicides bitertanol; fluotrimazole; triazbutil Urea Fungicides bentaluron; pencycuron; quinazamid Other Fungicides acibenzolar acypetacs allyl alcohol benzalkonium chloride benzamacril bethoxazin carvone chloropicrin DBCP dehydroacetic acid diclomezine diethyl pyrocarbonate fenaminosulf fenitropan fenpropidin formaldehyde furfural hexachlorobutadiene iodomethane isoprothiolane methyl bromide methyl isothiocyanate metrafenone nitrostyrene nitrothal-isopropyl OCH 2 phenylphenol phthalide piperalin probenazole proquinazid pyroquilon sodium orthophenylphenoxide spiroxamine sultropen thicyofen tricyclazole; chitin; chitosan; 4-cumylphenol, , 4-alpha-cumylphenol.

Examples of insecticides which can be mixed micronized metal formulations are shown in Table 2:

TABLE 2

| |
|---|
| Antibiotic Insecticides |
| allosamidin; thuringiensin; spinosad; abamectin; doramectin; emamectin eprinomectin; ivermectin; selamectin; milbemectin; milbemycin oxime; moxidectin |
| Botanical Insecticides |
| anabasine; azadirachtin; d-limonene; nicotine; pyrethrins cinerins; cinerin I; cinerin II; jasmolin I; jasmolin II; pyrethrin I; pyrethrin II; quassia; rotenone; ryania sabadilla |
| Carbamate Insecticides |
| bendiocarb; carbaryl; benfuracarb; carbofuran; carbosulfan; decarbofuran; furathiocarb; dimetan; dimetilan; hyquincarb; pirimicarb; alanycarb; aldicarb; aldoxycarb; butocarboxim; butoxycarboxim; methomyl; nitrilacarb; oxamyl; tazimcarb; thiocarboxime; thiodicarb; thiofanox; allyxycarb aminocarb; bufencarb; butacarb; carbanolate; cloethocarb; dicresyl; dioxacarb; EMPC; ethiofencarb; fenethacarb; fenobucarb; isoprocarb; methiocarb; metolcarb; mexacarbate; promacyl; promecarb; propoxur; trimethacarb; XMC; xylylcarb |
| Dinitrophenol Insecticides |
| dinex; dinoprop; dinosam; DNOC; cryolite; sodium hexafluorosilicate; sulfluramid |
| Formamidine Insecticides |
| amitraz; chlordimeform; formetanate; formparanate |
| Fumigant Insecticides |
| acrylonitrile; carbon disulfide; carbon tetrachloride; chloroform; chloropicrin; para-dichlorobenzene; 1,2-dichloropropane; ethyl formate; ethylene dibromide; ethylene dichloride; ethylene oxide; hydrogen cyanide; iodomethane; methyl bromide; methylchloroform; methylene chloride; naphthalene; phosphine; sulfuryl fluoride; tetrachloroethane |
| Insect Growth Regulators |
| bistrifluron; buprofezin; chlorfluazuron; cyromazine; diflubenzuron; flucycloxuron; flufenoxuron; hexaflumuron; lufenuron; novaluron; noviflumuron; penfluron; teflubenzuron; triflumuron; epofenonane; fenoxycarb; hydroprene; kinoprene; methoprene; pyriproxyfen; triprene; juvenile hormone I; juvenile hormone II; juvenile hormone III; chromafenozide; halofenozide; methoxyfenozide; tebufenozide; α-ecdysone; ecdysterone; diofenolan; precocene I; precocene II; precocene III; dicyclanil |
| Nereistoxin Analogue Insecticides |
| bensultap; cartap; thiocyclam; thiosultap; flonicamid; clothianidin; dinotefuran; imidacloprid; thiamethoxam; nitenpyram nithiazine; acetamiprid; imidacloprid; nitenpyram; thiacloprid |
| Organochlorine Insecticides |
| bromo-DDT; camphechlor; DDT; pp'-DDT; ethyl-DDD; HCH; gamma-HCH; lindane; methoxychlor; pentachlorophenol; TDE; aldrin; bromocyclen; chlorbicyclen; chlordane; chlordecone; dieldrin; dilor; endosulfan; endrin; HEOD; heptachlor; HHDN; isobenzan; isodrin; kelevan; mirex |
| Organophosphorus Insecticides |
| bromfenvinfos; chlorfenvinphos; crotoxyphos; dichlorvos; dicrotophos; dimethylvinphos; fospirate; heptenophos; methocrotophos; mevinphos; monocrotophos; naled; naftalofos; phosphamidon; propaphos; schradan; TEPP; tetrachlorvinphos; dioxabenzofos; fosmethilan; phenthoate; acethion; amiton; cadusafos; chlorethoxyfos; chlormephos; demephion; demephion-O; demephion-S; demeton; demeton-O; demeton-S; demeton-methyl; demeton-O-methyl; demeton-S-methyl; demeton-S-methylsulphon; disulfoton; ethion; ethoprophos; IPSP; isothioate; malathion; methacrifos; oxydemeton-methyl; oxydeprofos; oxydisulfoton; phorate; sulfotep; terbufos; thiometon; amidithion; cyanthoate; dimethoate; ethoate-methyl; formothion; mecarbam; omethoate; prothoate; sophamide; vamidothion chlorphoxim; phoxim; phoxim-methyl; azamethiphos; coumaphos; coumithoate; dioxathion; endothion; menazon; morphothion; phosalone; pyraclofos; pyridaphenthion; quinothion; dithicrofos; thicrofos; azinphos-ethyl; azinphos-methyl; dialifos; phosmet; isoxathion; zolaprofos; chlorprazophos; pyrazophos; chlorpyrifos; chlorpyrifos-methyl; butathiofos; diazinon; etrimfos; lirimfos; pirimiphos-ethyl; pirimiphos-methyl; primidophos; pyrimitate; tebupirimfos; quinalphos; quinalphos-methyl; athidathion; lythidathion; methidathion; prothidathion; isazofos; triazophos; azothoate; bromophos; bromophos-ethyl; carbophenothion; chlorthiophos; cyanophos; cythioate; dicapthon; dichlofenthion; etaphos; famphur; fenchlorphos; fenitrothion; fensulfothion; fenthion; fenthion-ethyl; heterophos; jodfenphos; mesulfenfos; parathion; parathion-methyl; phenkapton; phosnichlor; profenofos; prothiofos; sulprofos; temephos; trichlormetaphos-3; trifenofos; butonate; trichlorfon; |

TABLE 2-continued mecarphon; fonofos; trichloronat; cyanofenphos; EPN; leptophos; crufomate; fenamiphos; fosthietan; mephosfolan; phosfolan; pirimetaphos; acephate; isocarbophos; isofenphos; methamidophos; propetamphos; dimefox; mazidox; mipafox Oxadiazine Insecticides indoxacarb Phthalimide Insecticides dialifos; phosmet; tetramethrin Pyrazole Insecticides acetoprole; ethiprole; fipronil; tebufenpyrad; tolfenpyrad; vaniliprole Pyrethroid Insecticides acrinathrin; allethrin; bioallethrin; barthrin; bifenthrin; bioethanomethrin; cyclethrin; cycloprothrin; cyfluthrin; beta-cyfluthrin; cyhalothrin; gamma-cyhalothrin; lambda-cyhalothrin; cypermethrin; alpha-cypermethrin; beta-cypermethrin; theta-cypermethrin; zeta-cypermethrin; cyphenothrin; deltamethrin; dimefluthrin; dimethrin; empenthrin; fenfluthrin; fenpirithrin; fenpropathrin; fenvalerate; esfenvalerate; flucythrinate; fluvalinate; tau-fluvalinate; furethrin; imiprothrin; metofluthrin; permethrin; biopermethrin; transpermethrin; phenothrin; prallethrin; profluthrin; pyresmethrin; resmethrin; bioresmethrin; cismethrin; tefluthrin; terallethrin; tetramethrin; tralomethrin; transfluthrin; etofenprox; flufenprox; halfenprox; protrifenbute; silafluofen Pyrimidinamine Insecticides flufenerim; pyrimidifen Pyrrole Insecticides chlorfenapyr Tetronic Acid Insecticides spiromesifen Thiourea Insecticides diafenthiuron Urea Insecticides flucofuron; sulcofuron Other Insecticides closantel; clorpyrifos, crotamiton; EXD; fenazaflor; fenoxacrim; hydramethylnon; isoprothiolane; malonoben; metoxadiazone; nifluridide; pyridaben; pyridalyl; rafoxanide; triarathene; triazamate Examples of bactericides are shown in Table 3:

TABLE 3

Bactericides bronopol; 2-(thiocyanatomethylthio) benzothiazole (busan), cresol; dichlorophen; dipyrithione; dodicin; fenaminosulf; formaldehyde; hydrargaphen; 8-hydroxyquinoline sulfate; kasugamycin; nitrapyrin; octhilinone; oxolinic acid; oxytetracycline; probenazole; streptomycin; tecloftalam thiomersal. Isothiazolone-type bactericides such as, for example, Kathon 930, Kathon WT, Methylisothiazolinone, Benzisothiazolin-3-one and 2-octyl-3-isothiazolone.

Some preferred organic biocides are listed in Table 4 below:

TABLE 4

| Organic Biocides Useful for Wood Protection | |
|---|---|
| Name | Formula and CAS# |
| Azoles: | |
| Cyproconazole | $C_{15}H_{18}ClN_3O$: 94361-06-5 |
| Propiconazole | $C_{15}H_{17}Cl_2N_3O_2$: 60207-90-1 |
| Tebuconazole | $C_{16}H_{22}ClN_3O$: 107534-96-3 |
| Busan (TCMTB) | $C_9H_6N_2S_3$: 21564-17-0 |

TABLE 4-continued

| Organic Biocides Useful for Wood Protection | |
|---|---|
| Name | Formula and CAS# |
| 2-(thiocyanatomethylthio) benzothiazole | |
| Chlorothalonil | $C_8Cl_4N_2$: 1897-45-6 |
| Dichlofluanid | $C_9H_{11}Cl_2FN_2O_2S_2$: 1085-98-9 |
| Isothiazolone: | |
| Kathon 930 | $C_{11}H_{17}Cl_2NOS$: 64359-81-5 |
| Kathon WT | $C_4H_4ClNOS$: 26172-55-4 |
| Methylisothiazolinone | $C_4H_5NOS$: 2682-20-4 |
| Benzisothiazolin-3-one | $C_7H_5NOS$: 2634-33-5 |
| 2-octyl-3-isothiazolone | $C_{11}H_{19}NOS$: 26530-20-1 |
| Imidacloprid | $C_9H_{10}ClN_5O_2$: 138261-41-3 |
| Iodopropynyl Butylcarbamate (IPBC) | $C_8H_{12}INO_2$: 55406-53-6 |
| Pyrethroids: | |
| Bifenthrin | $C_{23}H_{22}ClF_3O_2$: 82657-04-3 |
| Cypermethrin | $C_{22}H_{19}Cl_2NO_3$: 52315-07-8 |
| Permethrin | $C_{21}H_{20}Cl_2O_3$: 52645-53-1 |
| Chitin | 1398-61-4 |
| Chitosan | 9012-76-4 |
| Clorpyrifos | $C_9H_{11}Cl_3NO_3PS$: 2921-88-2 |
| 4-cumylphenol | $C_{15}H_{16}O$: 599-64-4 |
| Fipronil | $C_{12}H_4Cl_2F_6N_4OS$: 120068-37-3 |
| Carbendazim | $C_9H_9N_3O_2$: 10605-21-7 |
| Cyfluthrin | $C_{22}H_{18}Cl_2FNO_3$: 68359-37-5 |

TABLE 4-continued

Organic Biocides Useful for Wood Protection

| Name | Formula and CAS# |
|---|---|
| 4-alpha-Cumylphenol | $C_{15}H_{16}O$: 599-64-4 |

Other biocides known by those skilled in the art that can optionally be used with the system would include insecticides, mold inhibitors, algaecides, bactericides and the like which may also be added to this system to further enhance the performance of this disclosure.

The insoluble biocides can be micronized into particles of submicron size ranging from 0.001 micrometers to 25 micrometers using a grinding mill. The particles are dispersed in standard dispersants such as acrylic copolymers, aqueous solution of copolymers with pigment affinity groups, modified polyacrylate, acrylic polymer emulsions, modified lignin and the like.

In one embodiment, micronized metal or metal compounds such as a copper compound is mixed with an insoluble micronized organic biocide. The metal or metal compound and the insoluble biocide may be micronized separately and then mixed or may be mixed first and then micronized.

In another embodiment, the metal compound is water soluble. Example of a suitable water soluble metal compounds are copper sulfate, copper acetate and copper nitrate. In this embodiment, an aqueous solution of the copper compound is prepared and then a micronized dispersion of an organic biocide is added to it.

Non-biocidal products such as water repellants (such as wax emulsions), colorants, emulsifying agents, dispersants, stabilizers, UV inhibitors, enhancing agents (such as trialkylamine oxides and alkoxylated diamines) and the like may also be added to the composition disclosed herein to further enhance the performance of the system or the appearance and performance of the resulting treated products. Those skilled in the art will recognize that some of these agents may also have some biocidal properties.

The trialkylamine oxides have the following structure.

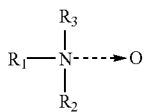

where $R_1$ is a linear or cyclic $C_8$ to $C_{40}$ saturated or unsaturated group and $R_2$ and $R_3$ independently are linear $C_1$ to $C_{40}$ saturated or unsaturated groups.

The alkoxylated diamines have the following structure:

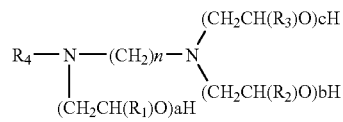

where n is an integer which can vary from 1 to 4, $R_1$, $R_2$ and $R_3$ are independently selected from the group consisting of hydrogen, methyl, ethyl and phenyl, and a, b and c are each integers which can be 1 to 6, and $R_4$ is fatty alkyl of $C_8$ to $C_{22}$.

Wood treated with the micronized preservatives of the present invention exhibits reduced leaching. Accordingly, if wood is treated with micronized copper, copper compounds, copper complexes or combinations thereof such that copper or copper ions are present at a concentration of greater than 0.001 pcf, the leaching of copper from the wood is less that 50% of leaching observed with non-micronized formulations. In another embodiment, at concentrations of copper or copper ions in treated wood greater than 0.001 pcf, the leaching of copper is less than 20% of leaching observed with non-micronized formulations. In yet another embodiment, at concentrations of copper or copper ions in treated wood between 0.001 and 0.05 pcf, the leaching of copper is less than 20% of leaching observed from wood containing greater than 0.001 pcf of non-micronized copper. Preferably, the leaching of copper is less 10%, and more preferably less than 5%, of leaching observed with non-micronized copper formulations when the concentration of copper or copper ions is between 0.001 to 0.5 pcf.

When wood is treated with micronized wood preservatives formulations disclosed herein, metal leaching is reduced. For example, as shown in FIG. 1A, when wood is treated with Cu-MEA composition the leaching of copper is about 12% and 24% respectively for 0.1 pcf (pounds per cubic feet) copper and 0.2 pcf copper. In contrast when the wood is treated with a micronized composition of the present invention the leaching was only about 2% and 1% respectively for the 0.1 pcf copper and 0.2 pcf copper. Copper leaching was evaluated following the procedures described in American Wood Preservers' Association Standard E11-97.

Similarly, FIG. 1B is a comparison of copper leaching from wood treated with a commercial copper based formulation ACQ-Type D and micronized copper carbonate plus dimethyldidecylammonium carbonate/bicarbonate (quat) at preservative retentions of 0.25 pcf and 0.40 pcf. The leaching test was conducted following the procedure described in AWPA Standard E11-97 "Standard Method of Determining the Leachability of Wood Preservatives". It can be seen that wood treated with micronized copper carbonate based formulation demonstrated much greater copper leaching resistance than the wood treated with the commercially available preservative Ammoniacal Copper Quat (ACQ)-Type D.

Also important is the penetration of the dispersion formulation into the wood's or other cellulose-based material's cellular structure. If the copper source used in formulating the dispersion formulation disclosed herein has a particle size in excess of 30 microns, the particles may be filtered by the surface of the wood and thus may not be uniformly distributed within the cell and cell wall. As shown in FIG. 2, the primary entry and movement of fluids through wood tissue occurs primarily through the tracheids and border pits. Tracheids have a diameter of about thirty microns. Fluids are transferred between wood cells by means of border pits.

The overall diameter of the border pit chambers typically varies from a several microns up to thirty microns while, the diameter of the pit openings (via the microfibrils) typically varies from several hundredths of a micron to several microns. FIG. 3 depicts the border pit structure for coniferous woods.

When wood is treated with micronized preservative formulation, if the particle size of the micronized preservative is less than the diameter of the pit openings, a complete penetration and a uniform distribution of micronized preservative in wood is expected. FIG. 4A depicts the complete copper penetration in wood treated with micronized copper hydroxide according to AWPA Standard A3-00 "Standard Method for Determining Penetration of Preservatives and Fire Retardants". A uniform blue was observed indicating the presence of copper. FIG. 4B depicts the complete copper penetration in wood treated with micronized copper carbonate plus quat.

Again, a uniform blue color was observed indicating the presence of copper. The determination of copper penetration was conducted following the procedures described in AWPA Standard A3-00 "Standard Method for Determining Penetration of Preservatives and Fire Retardants". FIG. 5 depicts the uniform particle distribution of cupric oxide through the cells of the wood treated with micronized CuO through the observation of Scanning Electron Microscope (SEM). The particles were confirmed to be copper compounds by the use of SEM-Energy Dispersed X-ray Analysis (EDXA).

Particle size of the metal, metal compounds or organic biocide used in the dispersion formulation disclosed herein typically does not exceed 30 microns or the metal and or organic biocide used in conjunction with the metal tends to be filtered by the surface of the wood thus not attaining a desired penetration and fluid flow through the wood tissue. In one embodiment particle size of the micronized particles used in the dispersion formulation disclosed herein can be between 0.001-10 microns. In another embodiment, the particle size is between 0.005 to 1.0 micron. In another embodiment, the particle size is between 0.05 to 10.0 microns. If a more uniform penetration is desired, particle size of the metal/metal compounds or the organic biocide used in the dispersion formulation disclosed herein can be between 0.05-1.0 microns.

The present invention also provides a method for preservation of wood. In one embodiment, the method comprises the steps of treating wood with a composition (treating fluid) comprising a dispersion of water insoluble micronized metal and/or metal compounds. In another embodiment, wood is treated with a composition comprising a dispersion of micronized metal and/or metal compounds and organic biocides, wherein the organic biocides are soluble or present as water insoluble micronized particles. The size of the micronized particles for the metal/metal compounds and organic biocide is between 0.001 to 25 microns, preferably between 0.005 to 10 microns, more preferably between 0.05 to 10 micron and even more preferably between 0.05 to 1.0 microns. In another embodiment, the wood is treated with a composition comprising soluble metal compounds and micronized organic biocides.

The present invention is not limited to applications which involve micronized particles which have been applied to wood as such. For example, the wood preservative effect of micronized particles can be realized by the formation of such particles in situ. By in situ, it is meant that particle formation takes place on or within the wood. Thus, the benefits of the present invention can be realized if particle formation takes place, for example, within the tracheids of the wood to be preserved. Additionally or instead, particle formation can take place outside of the tracheids, with the subsequent movement of at least some of the particles into the tracheids. Such a movement can be caused by, for example, pressure cycling, such as described in the examples. The micronized particles generally have an average size which is small enough to enable at least partial penetration of wood by particle migration through tracheids and border pits.

Thus, the present invention also provides a method for the preparation of wood containing the micronized particle preservative biocidal compositions of the present invention. The method comprises forming micronized particles of metal compound, biocide, or both, on or within the wood to be protected.

The treating fluid may be applied to wood by dipping, soaking, spraying, brushing, or any other means well known in the art. In a preferred embodiment, vacuum and/or pressure techniques are used to impregnate the wood in accord with this invention including the standard processes, such as the "Empty Cell" process, the "Modified Full Cell" process and the "Full Cell" process, and any other vacuum and/or pressure processes which are well known to those skilled in the art.

The standard processes are defined as described in AWPA Standard C1-03 "All Timber Products—Preservative Treatment by Pressure Processes". In the "Empty Cell" process, prior to the introduction of preservative, materials are subjected to atmospheric air pressure (Lowry) or to higher air pressures (Rueping) of the necessary intensity and duration. In the "Modified Full Cell", prior to introduction of preservative, materials are subjected to a vacuum of less than 77 kPa (22 inch Hg) (sea level equivalent). A final vacuum of not less than 77 kPa (22 inch Hg) (sea level equivalent) shall be used. In the "Full Cell Process", prior to introduction of preservative or during any period of condition prior to treatment, materials are subjected to a vacuum of not less than 77 kPa (22 inch Hg). A final vacuum of not less than 77 kPa (22 inch Hg) is used.

It should be understood that unless specifically set forth in conjunction with a method, the term "treatment" as used herein should not be construed as pertaining only to the application of micronized particles to wood which is to be preserved, but also includes in situ formation of micronized formation. Thus, the term "treatment," should generally be construed to encompass all methods as a result of which micronized particles are present in the wood. Thus, the term "treated wood" is only intended to mean wood comprising micronized particles, irrespective of the mode of formation/delivery of the micronized particles.

Furthermore, wood which contains a preservative composition of the present invention generally has the advantage of being less corrosive of nails and other metal implements than wood which contains other commonly used preservative compositions which contain amine compounds. Nails which contain iron, copper, nickel, (and other metals which would be used in nails and would have some susceptibility to alkaline corrosion) and/or other metals which are susceptible to alkaline corrosion will generally show some degree of corrosion after exposure to wood which contains non-micronized amine-containing preservative formulations. The same type nails when exposed to wood containing a micronized metal preservative can generally be expected to show less or no corrosion after an equivalent exposure period.

Moreover, in comparison to wood which has been treated with commonly available preservatives, wood which has been treated with micronized preservatives of the present invention is particularly resistant to mold growth. Without desiring to be bound by theory, it is thought that the amines and other nitrogenous compounds in currently used preservative compositions serve as an energy source for molds. Because the disclosed preservative compositions containing micronized copper are free of amines, wood which has been treated with them can be found to have less mold than wood which has been treated with other compositions and similarly exposed.

Wood which comprises micronized biocidal formulations generally exhibits reduced biocide leaching relative to wood which contains non-micronized biocidal compositions. Without desiring to be bound by theory, it is thought that the ability of a given component to be solvated in an aqueous environment is one of the most important considerations with respect to leaching. All other variables being equal, easily solvated compounds and ions exhibit greater leaching than chemical species which may not have the same ability to be solvated in a given aqueous environment. Thus, the presence of a biocide in micronized form prevents much of the biocide from being in direct contact with the aqueous environment, reducing its ability to be solvated. In environments which are conducive to leaching, the result is reduced leaching.

Wood treated with the compositions of the present invention has been observed to have a uniform distribution of micronized particles. This can be observed simply in the coloration (when a colored composition is used) or it can also be observed via the use of microscopy. For example, when scanning electron microscopy is combined with energy dispersive X-ray analysis (SEM-EDXA), the presence of, as well as the distribution of the micronized particles can be observed. SEM-EDXA is also useful for determination of the elements present in the micronized particles and therefore, the composition of the particles can be determined. Alternatively or additionally, specific staining methods can be carried out on SEM sections to determine the identity of the composition of the particles.

The following examples are provided to further describe certain embodiments of the invention but are in no way meant to limit the scope of the invention. Examples 1 through 5 demonstrate the formulation of the concentrated dispersions of copper compounds and the concentrated dispersions of copper compounds comprising various organic biocides. Examples 6 through 14 demonstrate the preparation of treating fluids using concentrated dispersions for the treatment of wood.

Example 1

500 g of copper hydroxide were added to a container containing 1091.7 grams of water and 75.0 grams of commercially available dispersants/wetting agents. The mixture was mechanically stirred for 5 minutes and then placed in a grinding mill. The sample was ground for about 30 minutes, and a stable dispersion containing about 30% copper hydroxide was obtained. The particle size of the copper hydroxide dispersion was analyzed by Horiba LA-910 Particle Size Distribution Analyzer (PSDA). The average particle size was 0.195 micrometers (um) with a distribution range of 0.04 um to 1.5 um.

Example 2

1000 grams of basic copper carbonate was mixed with 2158.3 grams of water and 175.0 grams of commercially available wetting agents/dispersants. The mixture was mechanically stirred for 10 minutes. The mixture was then placed in a grinding mill and ground for about 20 minutes. A stable dispersion was obtained with an average particle size of 0.199 micrometers.

Example 3

1000 grams of basic copper carbonate and 20 grams of tebuconazole were mixed with 3780 grams of water and 200 grams of wetting agents/dispersants. The mixture was mechanically stirred for about 10 minutes. The mixture was then placed in a grinding mill and ground for about 30 minutes. A stable dispersion containing 25% basic copper carbonate and 0.5% tebuconazole was obtained with an average particle size of 0.200 micrometers.

Example 4

300 grams of copper 8-hydroxyquinolate (Cu-8) were mixed with 855 grams of water and 45 grams of dispersants. The mixture was mechanically mixed for about 5 minutes and placed in a grinding mill. The mixture was ground for about 30 minutes and a stable dispersion containing 25% Cu-8 was obtained with an average particle size of 0.282 micrometers.

Example 5

A stable cupric oxide (CuO) dispersion containing about 30% CuO was supplied by Nanophase Technologies, Inc. The average particle size was about 0.1 micrometers. This can be mixed with organic soluble or micronized biocides.

Example 6

38.5 g of cupric hydroxide dispersion from Example 1 was mixed with 7.5 g of N,N-dimethyl-1-dodecylamine-N-oxide (AO) and 2954.0 g of water to produce a preservative treating fluid containing 0.385% cupric hydroxide and 0.25% AO. The fluid was then used to treat 2"×4"×10" samples of southern pine sapwood, and sealed with epoxy resin, using an initial vacuum of 28" Hg for 15 minutes, followed by a pressure cycle of 135 psi for 25 minutes and a final vacuum of 27" Hg for 10 minutes. The resulting treated wood was weighed and found to have doubled its weight. The treated sample was cut and the cross sections sprayed with a copper indicator to determine copper penetration following the procedure described in American Wood Preservers' Association Standard A3-00, and the blue color indicates the presence of copper. The sample was found to have 100% uniform distribution of copper throughout the cross section as in FIG. 4A. As a comparison, FIG. 4A also showed the cross section of untreated wood.

Example 7

50.0 g CuO dispersion from Example 5 were mixed with 2942.5 g of water and 7.5 g of didecyldimethylammonium chloride. The product was mixed until uniformly dispersed and the treating solution containing the following compositions was obtained:

| Components | Percent |
| --- | --- |
| Cupric Oxide | 0.50 |
| Didecyldimethylammonium Chloride | 0.25 |

A southern pine stake measuring 1.5"×3.5"×10" was placed in a laboratory retort with a vacuum of 27" Hg for 15 minutes. The treating solution was then pumped into the retort and the retort pressurized to 130 psi for 30 minutes. The solution was drained from the retort and the test stake weighed. Based on the weight pickup, the test stake doubled its weight and showed uniform penetration of the cupric oxide throughout the wood cross section. A sample taken from the center portion of the treated wood was submitted for scanning electron microscopy (SEM) analysis, and the SEM result indicated the uniform particle distribution in wood as shown in FIG. 5.

Example 8

4000 g of treating fluid containing 0.31% of cupric oxide and 0.16% didecyldimethylammonium carbonate were prepared by mixing CuO dispersion from Example 5 and didecyldimethylammonium carbonate. The fluid was used to treat 2"×4"×10" southern pine samples by placing the samples in a chamber and drawing a 27" Hg vacuum for 10 minutes. The treating fluid was then drawn into the chamber and allowed to stay in contact with the wood cubes for 15 minutes. The fluid was pumped from the chamber and the resulting wood had more than doubled its weight. Cross sections of the cubes showed 100% copper penetration.

Example 9

A preservative treating formulation was prepared by adding 0.15 kg of copper carbonate dispersion from Example 2 to 0.025 kg of a quaternary ammonium compound, dimethyl didecyl ammonium carbonate/bicarbonate and 4.825 kg of water. This fluid was allowed to mix until a homogenous fluid was prepared. This fluid was used to treat southern pine test stakes measuring 0.156×1.5×10.0 inches (4×38×254 mm) by the full-cell process. The resulting stakes showed a uniform distribution of copper throughout the wood cells. The treated test stakes were installed in the field to evaluate the field performance of the preservative following the procedure described in AWPA Standard E7-01 "Standard Method of Evaluating Wood Preservatives by Field Tests with Stakes". The test results indicated that the treated stakes were resistant to decay and insect attack. The fluid was also used to treat southern pine wood cube blocks measuring ¾"×¾"×¾" (19 mm×19 mm×19 mm). The treated cubes were exposed to several test fungi to evaluate the bio-efficacy of the preservative formulation following the procedure described in AWPA Standard E10-01 "Standard Method of Testing Wood Preservatives by Laboratory Soil-Block Cultures". Upon the completion of the soil-block test, the cubes were found to have less than 2.0% weight loss, indicating essentially no fungal attack to the treated cubes. In comparison, untreated wood cubes had approximately 50% weight loss after being exposed to the test fungi. The soil block test results indicated wood treated the above preservative formulation was resistant to fungal attack.

Example 10

A preservative treating composition was prepared by adding 0.1 kg of dispersion from Example 3 to 4.9 kg of water. The resulting fluid contained 0.50% copper carbonate and 0.01% tebuconazole. This fluid was then used to treat full-size lumber using the full-cell process wherein the wood is initially placed under a vacuum of 30" Hg for 30 minutes, followed by the addition of the treating solution. The system was then pressurized for 30 minutes at 110 psi. A final vacuum of 28" Hg for 30 minutes was applied to the wood to remove residual liquid. The wood was found to contain a uniform distribution of copper throughout the cross sections and is resistant to fungal and insect attack.

Example 11

54 g of dispersion from Example 3 and 7.5 g of N,N-dimethyl-1-hexadecylamine-N-oxide (AO) were mixed with 2938.5 grams of water to obtain a preservative treating fluid containing 0.45% carbonate, 0.009% tebuconazole and 0.25% AO. The resulting fluid was used to treat red pine lumber using a modified full-cell process. The resulting stakes were air-dried and found to a uniform distribution of copper throughout the cross sections and were resistant to fungal and insect attack.

Example 12

A preservative treating fluid was prepared by adding 16.0 g of Cu 8-hydroxyquinolate (Cu-8) dispersion from Example 4 to 3984.0 g of water. The resulting fluid contained 0.1% Cu-8.

The fluid was used to treat southern pine lumber using a full cell process. The treated stakes were oven dried and found to contain a uniform distribution of particles throughout the cross sections and were resistant to fungal and insect attack.

Example 13

A preservative treating fluid was prepared by mixing 175 g concentrated dispersion containing 20% copper carbonate and 0.5% cyproconazole with 3325.0 g water. The resulting solution contained 1.0% copper carbonate and 0.025% cyproconazole and was used to treat southern pine lumber using a full cell process. The treated stakes were oven dried and found to contain a uniform distribution of copper and cyproconazole throughout the cross sections and were resistant to fungal and insect attack.

Example 14

A preservative treating fluid can be prepared by mixing copper sulfate solution and micronized cyproconazole at a concentration of 0.25% Cu and 0.01% cyproconazole. The resulting fluid can be used to treat lumber using a full cell process. The treated sample can be air-dried for two weeks and tested for resistance to fungal and termite attack.

Example 15

Southern Pine wood was treated with a micronized copper carbonate dispersion from Example 9. Scanning electron microscopy with EDXA was performed by standard methods. Results are shown in FIG. 6. A uniform distribution of the micronized particles is observed. This examples indicates that the presence of micronized particles can be identified in treated wood and that the distribution of these particles was found to be uniform.

Although specific embodiments have been described herein, those skilled in the art will recognize that routine modifications can be made without departing from the spirit of the invention.

We claim:

1. Wood comprising an aqueous wood preservative composition, wherein the composition comprises:
   (a) a biocidally effective amount of particles of a copper compound with a particle size of between 0.001 and 1.0 microns, dispersed in water; and
   (b) a biocidally effective amount of one or more organic biocides;
   wherein the copper compound is selected from the group consisting of copper hydroxide, cupric oxide, cuprous oxide, copper carbonate, basic copper carbonate, copper oxychloride, copper dimethyldithiocarbamate, copper omadine, and copper borate, and
   wherein the particles of the copper compound are obtained by milling, distributed throughout a cross-section of the wood, and render the wood resistant to fungal decay.

2. The wood of claim 1, wherein the organic biocide is selected from a group consisting of fungicide, insecticide, algaecide, moldicide, and bactericide.

3. The wood of claim 1, wherein the organic biocide is an azole, a borate, or a fluoride.

4. The wood of claim 3, wherein the organic biocide is an azole.

5. The wood of claim 4, wherein the azole is tebuconazole.

6. The wood of claim 1, wherein the organic biocide is a solid.

7. The wood of claim 6, wherein the organic biocide has a particle size of between 0.001 and 25 microns.

8. The wood of claim 7, wherein the organic biocide is tebuconazole.

9. The wood of claim 1, wherein the wood comprises coniferous wood.

10. The wood of claim 9, wherein the coniferous wood comprises southern pine.

11. The wood of claim 1, wherein the particles of copper compound are uniformly distributed throughout a cross-section of the wood.

12. The wood of claim 11, wherein copper leaching from the wood is reduced as compared to copper leaching from a wood comprising copper monoethanolamine complex.

13. The wood of claim 1, wherein the wood is lumber.

14. Wood comprising an aqueous wood preservative composition, wherein the composition comprises:
   (a) a biocidally effective amount of particles of a copper compound with a particle size of between 0.001 and 1.0 microns, dispersed in water; and
   (b) a biocidally effective amount of one or more organic biocides;
   wherein the copper compound is selected from the group consisting of copper hydroxide, cupric oxide, cuprous oxide, copper carbonate, basic copper carbonate, copper oxychloride, copper dimethyldithiocarbamate, copper omadine, and copper borate,
   wherein the particles of the copper compound are distributed throughout a cross-section of the wood and render the wood resistant to fungal decay, and
   wherein copper leaching from the wood is reduced as compared to copper leaching from a wood comprising copper monoethanolamine complex.

15. The wood of claim 14, wherein the organic biocide is selected from a group consisting of fungicide, insecticide, algaecide, moldicide, and bactericide.

16. The wood of claim 14, wherein the organic biocide is an azole, a borate, or a fluoride.

17. The wood of claim 16, wherein the organic biocide is an azole.

18. The wood of claim 17, wherein the azole is tebuconazole.

19. The wood of claim 14, wherein the organic biocide is a solid.

20. The wood of claim 19, wherein the organic biocide has a particle size of between 0.001 and 25 microns.

21. The wood of claim 20, wherein the organic biocide is tebuconazole.

22. The wood of claim 14, wherein the wood comprises coniferous wood.

23. The wood of claim 22, wherein the coniferous wood comprises southern pine.

24. The wood of claim 14, wherein the particles of copper compound are uniformly distributed throughout a cross-section of the wood.

25. The wood of claim 14, wherein the wood is lumber.

* * * * *